(12) United States Patent
Helfer et al.

(10) Patent No.: US 6,930,242 B1
(45) Date of Patent: *Aug. 16, 2005

(54) MAGNETICALLY SHIELDED CONDUCTOR

(75) Inventors: Jeffrey L. Helfer, Webster, NY (US);
Xingwu Wang, Wellsville, NY (US)

(73) Assignee: Nanoset, LLC, East Rochester, NY (US)

(*) Notice: Subject to any disclaimer, the term of this patent is extended or adjusted under 35 U.S.C. 154(b) by 575 days.

This patent is subject to a terminal disclaimer.

(21) Appl. No.: 10/090,553

(22) Filed: Mar. 4, 2002

Related U.S. Application Data

(63) Continuation-in-part of application No. 10/054,407, filed on Jan. 22, 2002, now Pat. No. 6,506,972.

(51) Int. Cl.[7] .............................................. H01B 11/06
(52) U.S. Cl. ................... 174/36; 174/102 SC
(58) Field of Search .................. 174/36, 120 SC, 174/113 R, 102 SC; 333/12, 243

(56) References Cited

U.S. PATENT DOCUMENTS

| | | | | | |
|---|---|---|---|---|---|
| 5,927,621 | A | * | 7/1999 | Ziolo et al. ................... 241/21 |
| 6,225,565 | B1 | * | 5/2001 | Prysner ................ 174/120 SC |
| 6,506,972 | B1 | * | 1/2003 | Wang .......................... 174/36 |
| 6,673,999 | B1 | * | 1/2004 | Wang et al. .................. 174/36 |
| 6,765,144 | B1 | * | 7/2004 | Wang et al. .................. 174/36 |
| 6,768,053 | B1 | * | 7/2004 | Wang et al. .................. 174/36 |

* cited by examiner

*Primary Examiner*—Chau N. Nguyen
(74) *Attorney, Agent, or Firm*—Howard J. Greenwald; Peter J. Mikesell

(57) ABSTRACT

A conductor assembly that contains a flexible conductor and a layer of nanomagnetic material coated onto the conductor. The layer of nanomagnetic material has a tensile modulus of elasticity of at least about $15 \times 10^6$ pounds per square inch, an average particle size of less than 100 nanometers, a saturation magnetization of from about 200 to about 26,000 Gauss, and a thickness of less than about 2 microns.

20 Claims, 35 Drawing Sheets

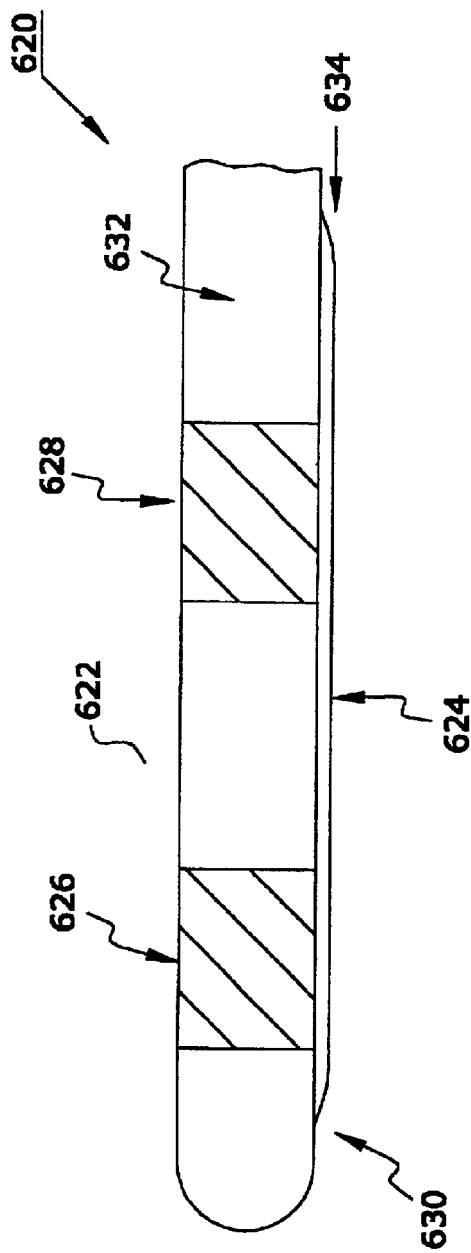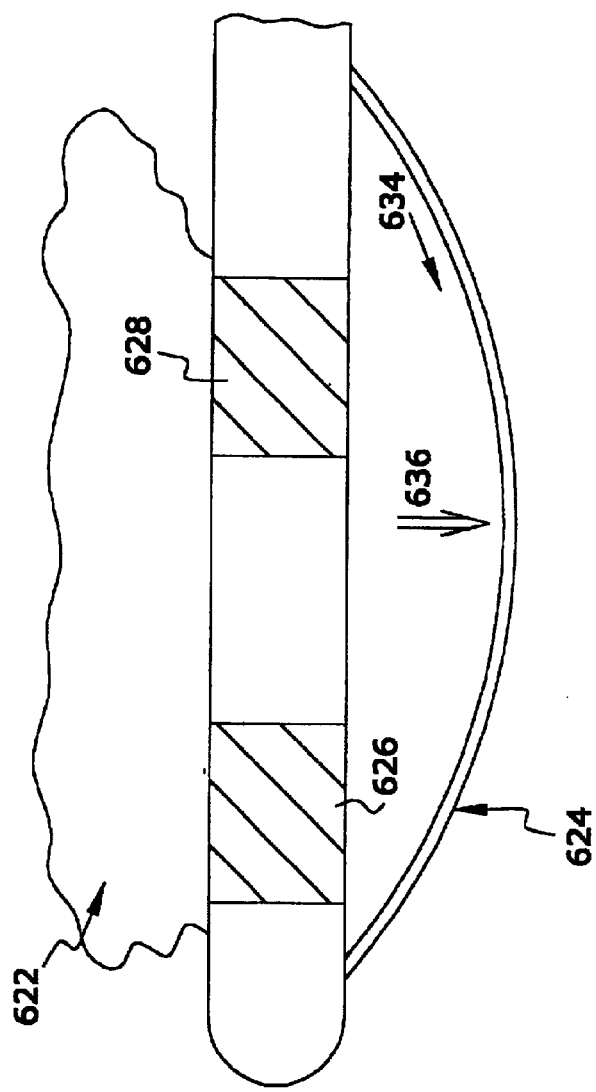
FIG.16E
FIG.16F

MAGNETICALLY SHIELDED CONDUCTOR

CROSS-REFERENCE TO RELATED PATENT APPLICATION

This patent application is a continuation-in-part of applicants' patent application U.S. Ser. No. 10/054,407, filed on Jan. 22, 2002, now U.S. Pat. No. 6,506,972.

FIELD OF THE INVENTION

A conductor assembly comprised of a conductor assembly disposed within an insulating sheath, wherein the sheath is coated with nanomagnetic material.

BACKGROUND OF THE INVENTION

Many implanted medical devices that are powered by electrical energy have been developed. Most of these devices comprise a power source, one or more conductors, and a load.

When a patient with one of these implanted devices is subjected to high intensity magnetic fields, currents are often induced in the implanted conductors. The large current flows so induced often create substantial amounts of heat. Because living organisms can generally only survive within a relatively narrow range of temperatures, these large current flows are dangerous.

Furthermore, implantable devices, such as implantable pulse generators (IPGs) and cardioverter defibrillator/pacemaker (CDPs), are sensitive to a variety of forms of electromagnetic interference (EMI). These devices include sensing and logic systems that respond to low-level signals from the heart. Because the sensing systems and conductive elements of these implantable devices are responsive to changes in local electromagnetic fields, they are vulnerable to external sources of severe electromagnetic noise, and in particular to electromagnetic fields emitted during magnetic resonance imaging (MRI) procedures. Therefore, patients with implantable devices are generally advised not to undergo magnetic resonance imaging (MRI) procedures, which often generate magnetic fields of from between about 1 about 20 Teslas.

One additional problem with implanted conductors is that, when they are conducting electricity and are simultaneously subjected to large magnetic fields, a Lorentz force is created which often causes the conductor to move. This movement may damage body tissue.

In U.S. Pat. No. 4,180,600, there is disclosed and claimed a fine magnetically shielded conductor wire consisting of a conductive copper core and a magnetically soft alloy metallic sheath metallurgically secured to the conductive core, wherein the sheath consists essentially of from 2 to 5 weight percent of molybdenum, from about 15 to about 23 weight percent of iron, and from about 75 to about 85 weight percent of nickel. Although the device of this patent does provide magnetic shielding, it still creates heat when it interacts with strong magnetic fields.

It is an object of this invention to provide a conductor assembly, which is shielded from large magnetic fields, which does not create large amounts of heat in the presence of such fields, and which does not exhibit the Lorentz effect when subjected to such fields.

SUMMARY OF THE INVENTION

In accordance with this invention, there is provided a magnetically shielded conductor assembly comprised of a first conductor disposed within an insulating matrix, wherein said insulating matrix is coated with a nanomagnetic particulate material.

BRIEF DESCRIPTION OF THE DRAWINGS

The invention will be described by reference to the following drawings, in which like numerals refer to like elements, and in which.

DESCRIPTION OF THE PREFERRED EMBODIMENTS

This specification is divided into two separate sections. In the first section of the case, a coated conductor assembly is described. In the second section of the case, a multiplicity of devices comprised of coated elements are described.

Figure 1:
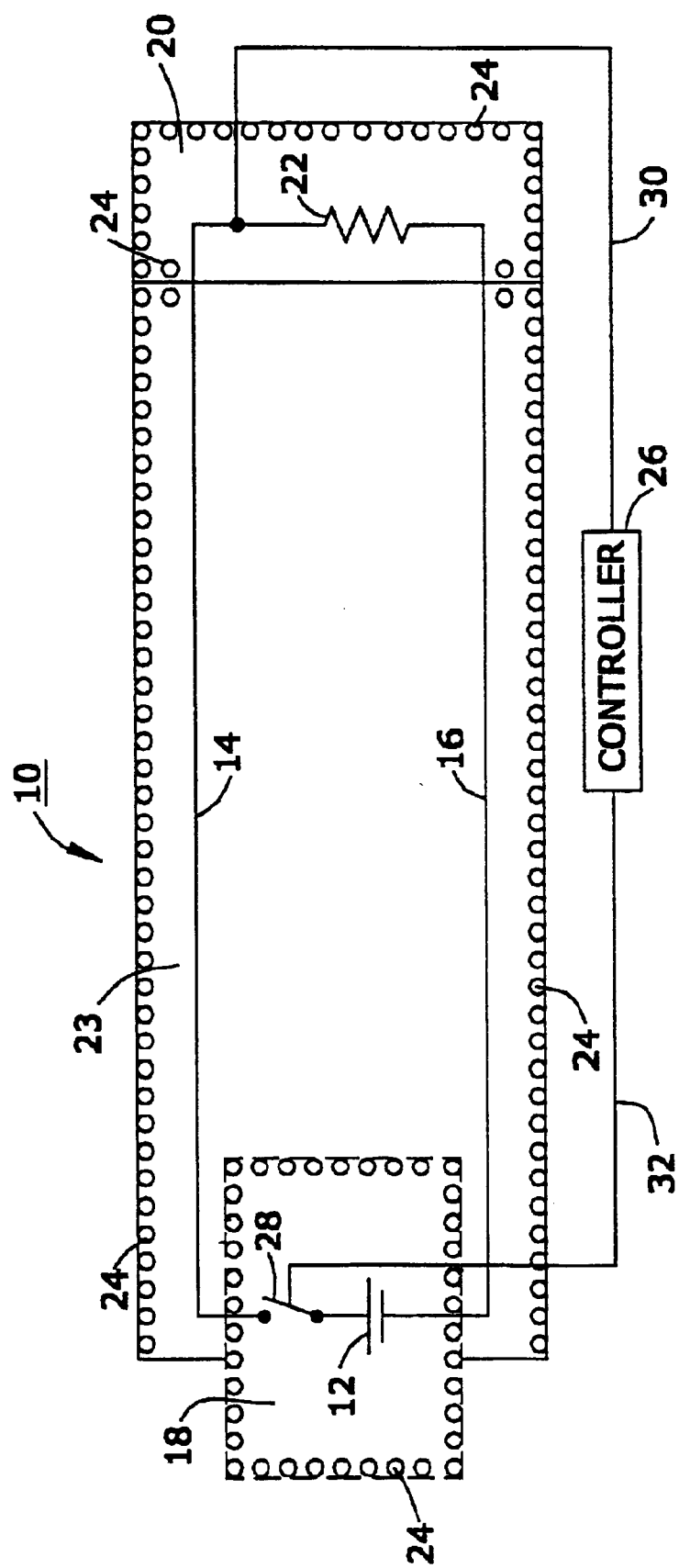
FIG. 1 is a schematic sectional view of a shielded implanted device comprised of the conductor assembly of this of his invention.

FIG. 1 is a schematic sectional view of one preferred device 10 that, in one embodiment, is implanted in a living organism. Referring to FIG. 1, it will be seen that device 10 is comprised of a power source 12, a first conductor 14, a second conductor 16, a first insulative shield 18 disposed about power source 12, a second insulative shield 20 disposed about a load 22, a third insulative shield 23 disposed about a first conductor 14, and a second conductor 16, and a multiplicity of nanomagentic particles 24 disposed on said first insulative shield, said second insulative shield, and said third insulative shield.

In the embodiment depicted in FIG. 1, the power source 12 is a battery 12 that is operatively connected to a controller 26. In the embodiment depicted, controller 26 is operatively connected to the load 22 and the switch 28. Depending upon the information finished to controller 26, it may deliver no current, direct current, and/or current pulses to the load 22.

In one embodiment, not shown, the controller 26 and/or the wires 30 and 32 are shielded from magnetic radiation. In another embodiment, not shown, one or more connections between the controller 26 and the switch 28 and/or the load 22 are made by wireless means such as, e.g., telemetry means.

In one embodiment, not shown, the power source 12 provides a source of alternating current. In another embodiment, the power source 12 in conjunction with the controller 26 provides pulsed direct current.

The load 22 may be any of the implanted devices known to those skilled in the art. Thus, e.g., load 22 may be a pacemaker. Thus, e.g., load 22 may be an artificial heart. Thus, e.g., load 22 may be a heart-massaging device. Thus, e.g., load 22 may be a defibrillator.

The conductors 14 and 16 may be any conductive material(s) that have a resistivity at 20 degrees Centigrade of from about 1 to about 100 microohm-centimeters. Thus, e.g., the conductive material(s) may be silver, copper, aluminum, alloys thereof, mixtures thereof, and the like.

In one embodiment, the conductors 14 and 16 consist essentially of such conductive material. Thus, e.g., it is preferred not to use, e.g., copper wire coated with enamel. The use of such typical enamel coating on the conductor does not work well in the instant invention.

In the first step of the process of this invention, step 40, the conductive wires 14 and 16 are coated with electrically insulative material. Suitable insulative materials include nano-sized silicon dioxide, aluminum oxide, cerium oxide, yttrium-stabilized zirconia, silicon carbide, silicon nitride, aluminum nitride, and the like. In general, these nano-sized particles will have a particle size distribution such that at least about 90 weight percent of the particles have a maximum dimension in the range of from about 10 to about 100 nanometers.

The coated conductors 14 and 16 may be prepared by conventional means such as, e.g., the process described in U.S. Pat. No. 5,540,959, the entire disclosure of which is hereby incorporated by reference into this specification. This patent describes and claims a process for preparing a coated substrate, comprising the steps of: (a) creating mist particles from a liquid, wherein: 1. said liquid is selected from the group consisting of a solution, a slurry, and mixtures thereof, 2. said liquid is comprised of solvent and from 0.1 to 75 grams of solid material per liter of solvent, 3. at least 95 volume percent of said mist particles have a maximum dimension less than 100 microns, and 4. said mist particles are created from said first liquid at a rate of from 0.1 to 30 milliliters of liquid per minute; (b) contacting said mist particles with a carrier gas at a pressure of from 761 to 810 millimeters of mercury; (c) thereafter contacting said mist particles with alternating current radio frequency energy with a frequency of at least 1 megahertz and a power of at least 3 kilowatts while heating said mist particles to a temperature of at least about 100 degrees centigrade, thereby producing a heated vapor, (d) depositing said heated vapor onto a substrate, thereby producing a coated substrate; and (e) subjecting said coated substrate to a temperature of from about 450 to about 1,400 degrees centigrade for at least about 10 minutes.

By way of further illustration, one may coat conductors 14 and 16 by means the processes disclosed in a text by D. Satas on "Coatings Technology Handbook" (Marcel Dekker, Inc., New York, N.Y., 1991). As is disclosed in such text, one may use cathodic arc plasma deposition (see pages 229 et seq.), chemical vapor deposition (see pages 257 et seq.), sol-gel coatings (see pages 655 et seq.), and the like.

Figure 2:
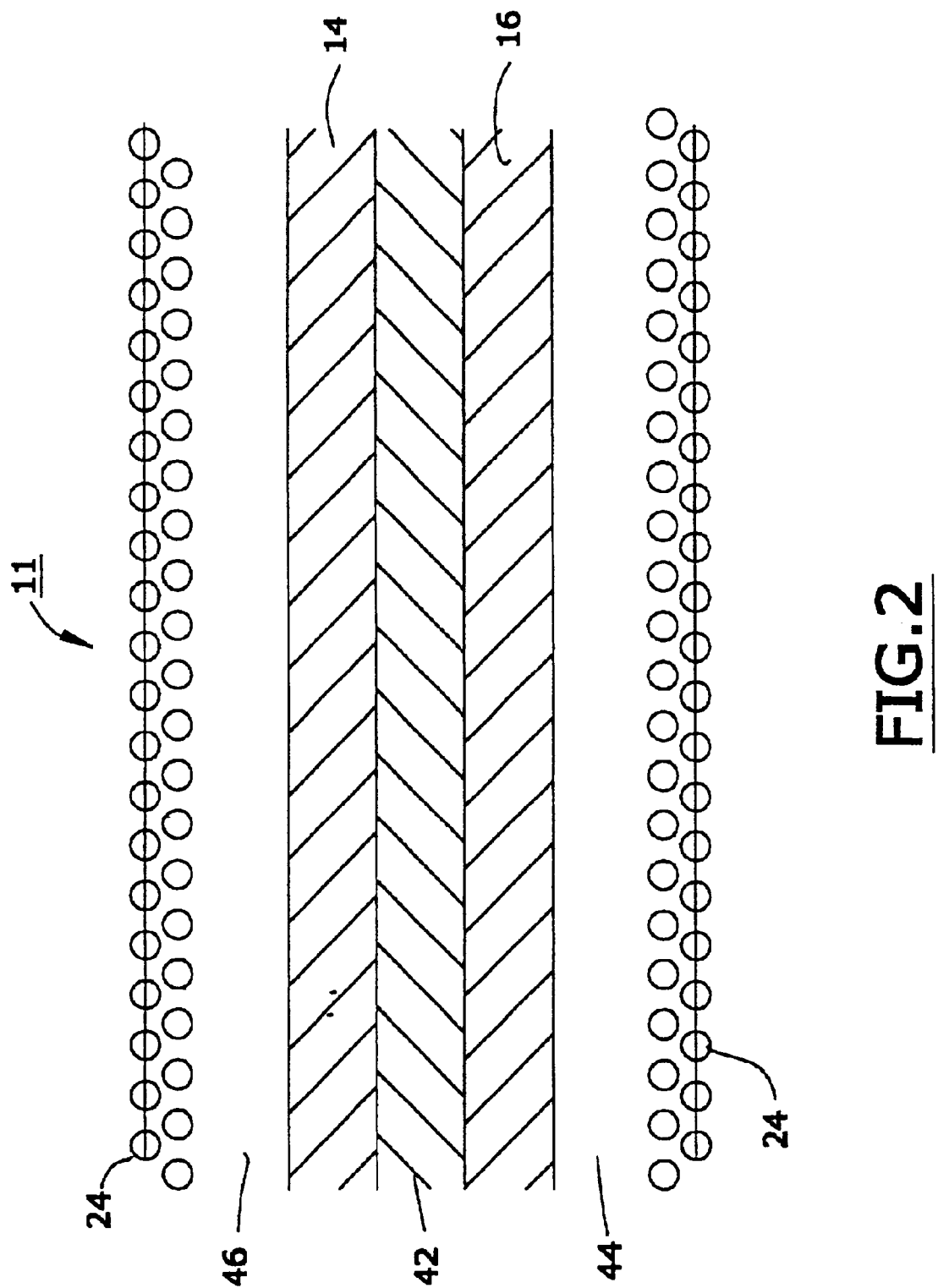
FIG. 2 is an enlarged sectional view of a portion of the conductor assembly of FIG. 1.

FIG. 2 is a sectional view of the coated conductors 14/16 of the device of FIG. 1. Referring to FIG. 2, it will be seen that conductors 14 and 16 are separated by insulating material 42. In order to obtain the structure depicted in FIG. 2, one may simultaneously coat conductors 14 and 16 with the insulating material so that such insulators both coat the conductors 14 and 16 and fill in the distance between them with insulation.

The insulating material 42, that is disposed between conductors 14/16, may be the same as the insulating material 44/46 that is disposed above conductor 14 and below conductor 16. Alternatively, and as dictated by the choice of processing steps and materials, the insulating material 42 may be different from the insulating material 44 and/or the insulating material 46. Thus, step 48 of the process describes disposing insulating material between the coated conductors 14 and 16. This step may be done simultaneous with step 40; and if may be done thereafter.

The insulating material 42, the insulating material 44, and the insulating material 46 each generally has a resistivity of from about 1,000,000,000 to about 10,000,000,000,000 ohm-centimeter.

After the insulating material 42/44/46 has been deposited, and in one embodiment, the coated conductor assembly is heat treated in step 50. This heat treatment often is used in conjunction with coating processes in which the heat is required to bond the insulative material to the conductors 14/16.

The heat-treatment step may be conducted after the deposition of the insulating material 42/44/46, or it may be conducted simultaneously therewith. In either event, and when it is used, it is preferred to heat the coated conductors 14/16 to a temperature of from about 200 to about 600 degrees Centigrade for from about 1 minute to about 10 minutes.

Figure 1A:
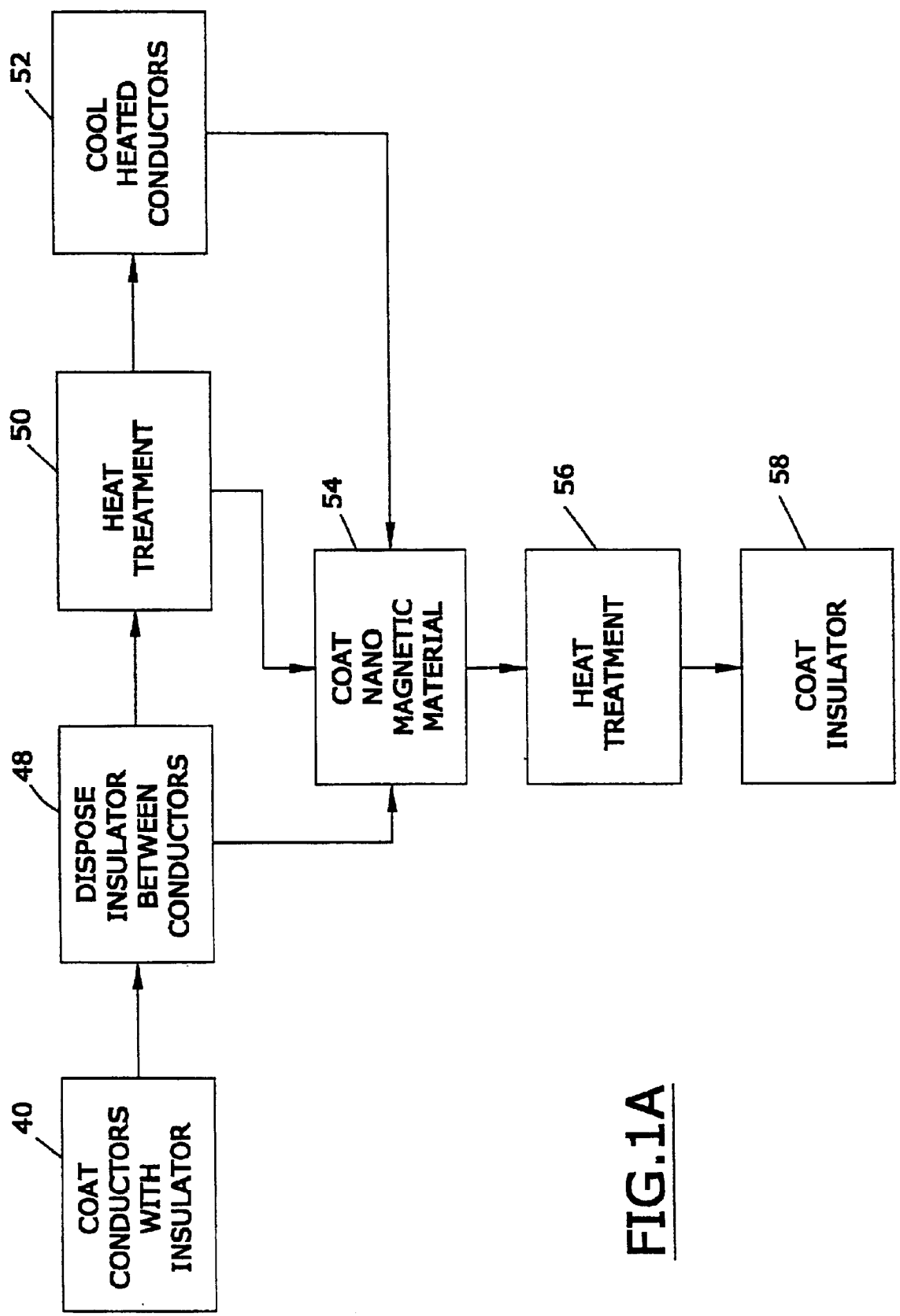
FIG. 1A is a flow diagram of a preferred process of the invention.

Referring again to FIG. 1A, and in step 52 of the process, after the coated conductors 14/16 have been subjected to heat treatment step 50, they are allowed to cool to a temperature of from about 30 to about 100 degrees Centigrade over a period of time of from about 3 to about 15 minutes.

One need not invariably heat treat and/or cool. Thus, referring to FIG. 1A, one may immediately coat nanomagentic particles onto to the coated conductors 14/16 in step 54 either after step 48 and/or after step 50 and/or after step 52.

In step 54, nanomagnetic materials are coated onto the previously coated conductors 14 and 16. This best shown in FIG. 2, wherein the nanomagnetic particles are identified as particles 24.

In general, and as is known to those skilled in the art, nanomagnetic material is magnetic material which has an average particle size less than 100 nanometers and, preferably, in the range of from about 2 to 50 nanometers.

Reference may be had, e.g., to U.S. Pat. No. 5,889,091 (rotationally free nanomagnetic material), U.S. Pat. Nos. 5,714,136, 5,667,924, and the like. The entire disclosure of each of these United States patents is hereby incorporated by reference into this specification.

The nanomagnetic materials may be, e.g., nano-sized ferrites such as, e.g., the nanomagnetic ferrites disclosed in U.S. Pat. No. 5,213,851, the entire disclosure of which is hereby incorporated by reference into this specification. This patent claims a process for coating a layer of ferritic material with a thickness of from about 0.1 to about 500 microns onto a substrate at a deposition rate of from about 0.01 to about 10 microns per minute per 35 square centimeters of substrate surface, comprising the steps of: (a) providing a solution comprised of a first compound and a second compound, wherein said first compound is an iron compound and said second compound is selected from the group consisting of compounds of nickel, zinc, magnesium, strontium, barium, manganese, lithium, lanthanum, yttrium, scandium, samarium, europium, terbium, dysprosium, holmium, erbium, ytterbium, lutetium, cerium, praseodymium, thulium, neodymium, gadolinium, aluminum, iridium, lead, chromium, gallium, indium, chromium, samarium, cobalt, titanium, and mixtures thereof, and wherein said solution is comprised of from about 0.01 to about 1,000 grams of a mixture consisting essentially of said compounds per liter of said solution; (b) subjecting said solution to ultrasonic sound waves at a frequency in excess of 20,000 hertz, and to an atmospheric pressure of at least about 600 millimeters of mercury, thereby causing said solution to form into an aerosol; (c) providing a radio frequency plasma reactor comprised of a top section, a bottom section, and a radio-frequency coil; (d) generating a hot plasma gas within said radio frequency plasma reactor, thereby producing a plasma region; (e) providing a flame region disposed above said top section of said radio frequency plasma reactor, (f) contacting said aerosol with said hot plasma gas within said plasma reactor while subjecting said aerosol to an atmospheric pressure of at least about 600 millimeters of mercury and to a radio frequency alternating current at a frequency of from about 100 kilohertz to about 30 megahertz, thereby forming a vapor; (g) providing a substrate disposed above said flame region; and (h) contacting said vapor with said substrate, thereby forming said layer of ferritic material.

By way of further illustration, one may use the techniques described in an article by M. De Marco, X. W. Wang, et al. on "Mossbauer and magnetization studies of nickel ferrites" published in the Journal of Applied Physics 73(10), May 15, 1993, at pages 6287–6289.

In general, the thickness of the layer of nanomagnetic material deposited onto the coated conductors 14/16 is less than about 5 microns and generally from about 0.1 to about 3 microns.

After the nanomagnetic material is coated in step 54, the coated assembly may be optionally heat-treated in step 56. In this optional step 56, it is preferred to subject the coated conductors 14/16 to a temperature of from about 200 to about 600 degrees Centigrade for from about 1 to about 10 minutes.

Figure 3:
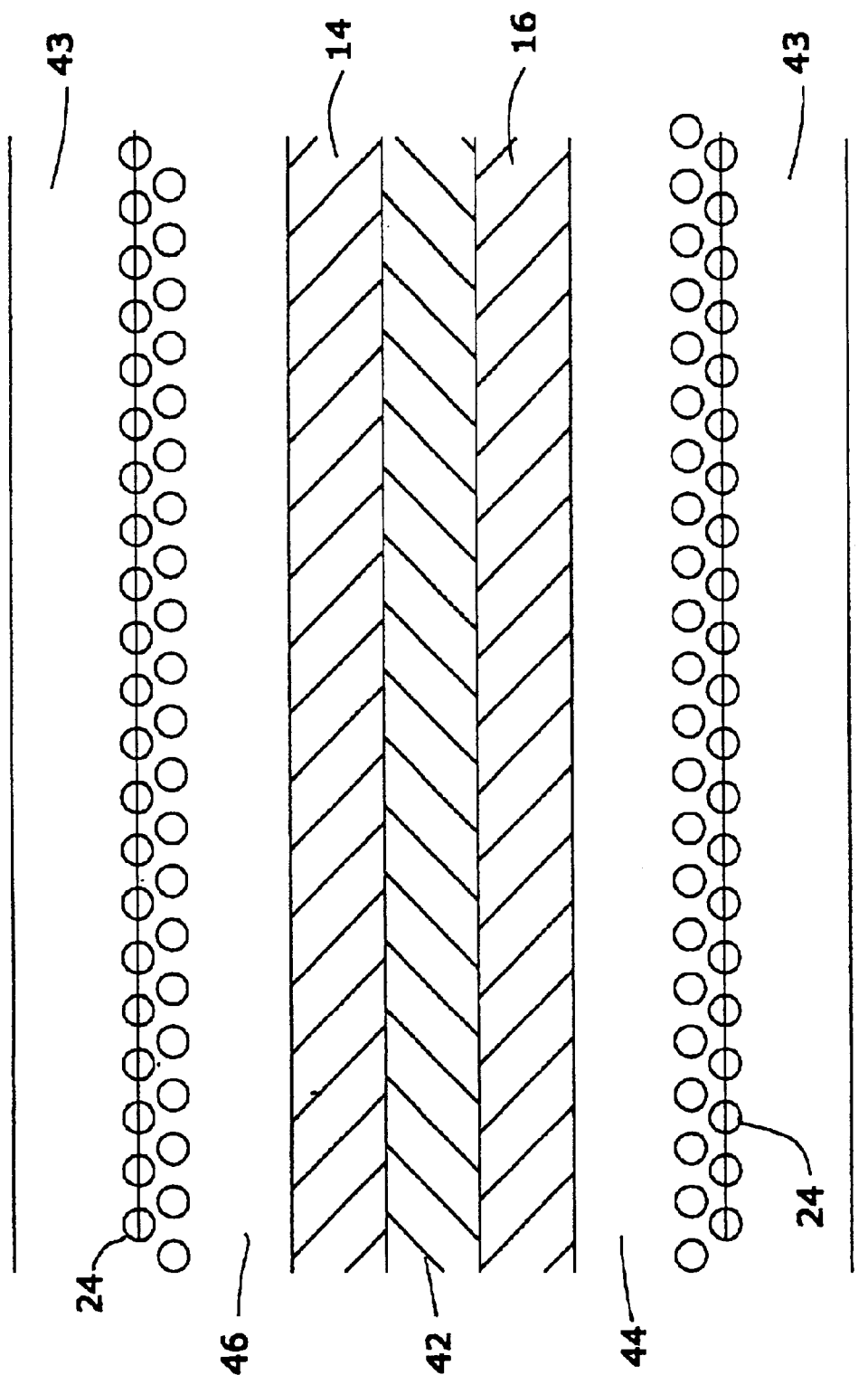
FIG. 3 is a sectional view of another conductor assembly of this invention.

In one embodiment, illustrated in FIG. 3, additional insulating layers 43 are coated onto the assembly depicted in FIG. 2, by one or more of the processes disclosed hereinabove. This is conducted in optional step 58 (see FIG. 1A).

Figure 4:
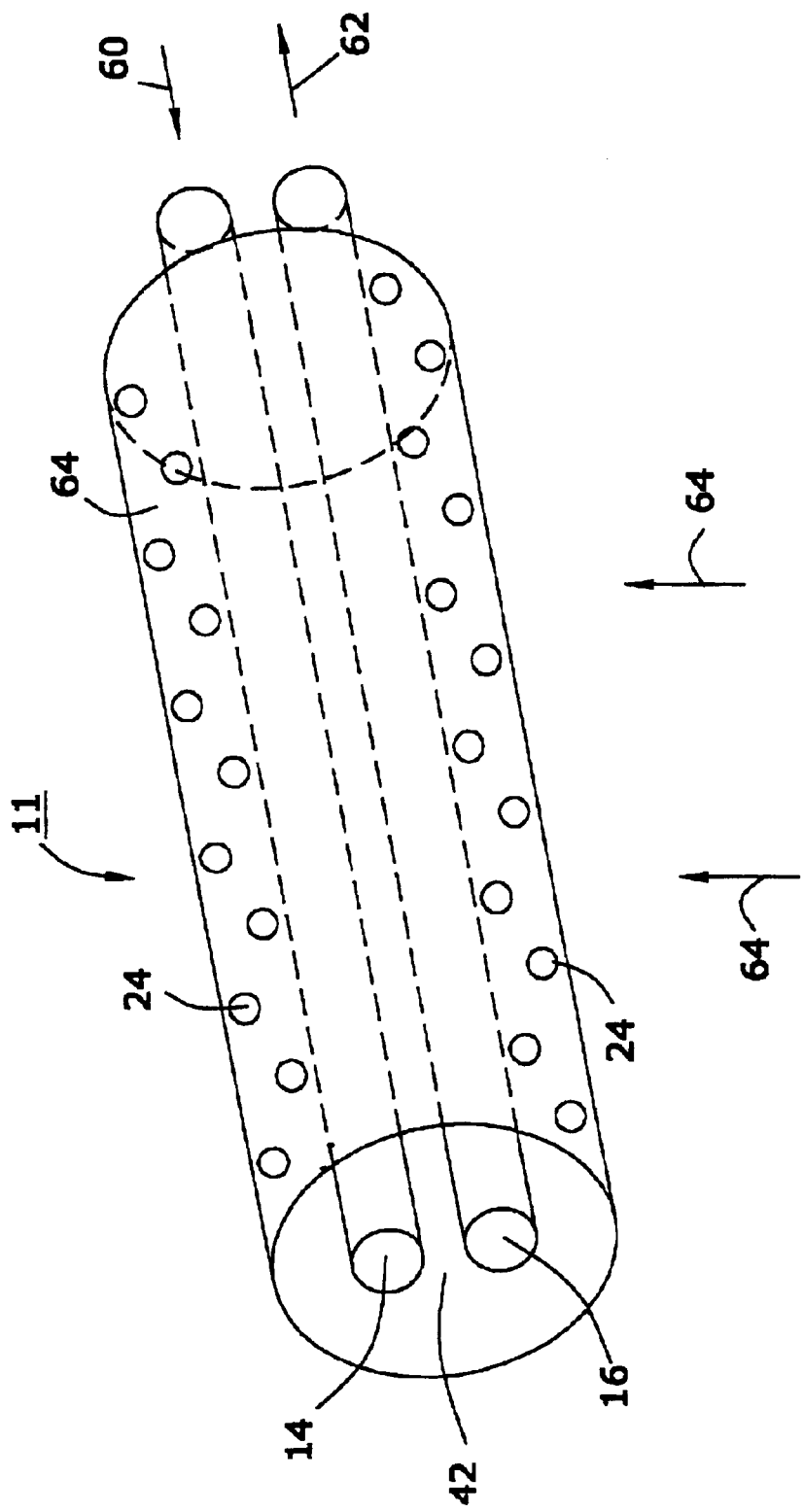
FIG. 4 is a schematic view of the conductor assembly of FIG. 2.

FIG. 4 is a partial schematic view of the assembly 11 of FIG. 2, illustrating the current flow in such assembly. Referring go FIG. 4, it will be seen that current flows into conductor 14 in the direction of arrow 60, and it flows out of conductor 16 in the direction of arrow 62. The net current flow through the assembly 11 is zero; and the net Lorentz force in the assembly 11 is thus zero. Consequently, even high current flows in the assembly 11 do not cause such assembly to move.

In the embodiment depicted in FIG. 4, conductors 14 and 16 are substantially parallel to each other. As will be apparent, without such parallel orientation, there may be some net current and some net Lorentz effect.

In the embodiment depicted in FIG. 4, and in one preferred aspect thereof, the conductors 14 and 16 preferably have the same diameters and/or the same compositions and/or the same length.

Referring again to FIG. 4, the nanomagnetic particles 24 are present in a density sufficient so as to provide shielding from magnetic flux lines 64. Without wishing to be bound to any particular theory, applicant believes that the nanomagnetic particles 24 trap and pin the magnetic lines of flux 64.

In order to function optimally, the nanomagnetic particles 24 have a specified magnetization. As is known to those skilled in the art, magnetization is the magnetic moment per unit volume of a substance. Reference may be had, e.g., to U.S. Pat. Nos. 4,169,998, 4,168,481, 4,166,263, 5,260,132, 4,778,714, and the like. The entire disclosure of each of these United States patents is hereby incorporated by reference into this specification.

Referring again to FIG. 4, the layer of nanomagnetic particles 24 preferably has a saturation magnetization, at 25 degrees Centigrade, of from about 200 to about 25,000 Gauss, or higher. In one embodiment, the saturation magnetization at room temperature of the nanomagentic particles is from about 500 to about 10,000 Gauss. For a discussion of the saturation magnetization of various materials, reference may be had, e.g., to U.S. Pat. Nos. 4,705,613, 4,631, 613, 5,543,070, 3,901,741 (cobalt, samarium, and gadolinium alloys), and the like. The entire disclosure of each of these United States patents is hereby incorporated by reference into this specification. As will be apparent to those skilled in the art, especially upon studying the aforementioned patents, the saturation magnetization of thin films is often higher than the saturation magnetization of bulk objects.

In one embodiment, it is preferred to utilize a thin film with a thickness of less than about 2 microns and a saturation magnetization in excess of 20,000 Gauss. The thickness of the layer of nanomagentic material is measured from the bottom surface of the layer that contains such material to the top surface of such layer that contains such material; and such bottom surface and/or such top surface may be contiguous with other layers of material (such as insulating material) that do not contain nanomagnetic particles.

Thus, e.g., one may make a thin film in accordance with the procedure described at page 156 of Nature, Volume 407, Sep. 14, 2000, that describes a multilayer thin film has a saturation magnetization of 24,000 Gauss.

By the appropriate selection of nanomagnetic particles, and the thickness of the films deposited, one may obtain saturation magnetizations of as high as at least about 26,000.

In the preferred embodiment depicted in FIG. 4, the nanomagnetic particles 24 are disposed within an insulating matrix 64 so that any heat produced by such particles will be slowly dispersed within such matrix. Such matrix, as indicated hereinabove, may be made from ceria, calcium oxide, silica, alumina. In general, the insulating material 42 preferably has a thermal conductivity of less than about 20

(caloriescentimeters/square centimeters–degree second)× 10,000. See, e.g., page E-6 of the 63$^{rd}$ Edition of the "Handbook of Chemistry and Physics" (CRC Press, Inc., Boca Raton, Fla., 1982).

The nanomagnetic materials 24 typically comprise one or more of iron, cobalt, nickel, gadolinium, and samarium atoms. Thus, e.g., typical nanomagnetic materials include alloys of iron and nickel (permalloy), cobalt, niobium, and zirconium (CNZ), iron, boron, and nitrogen, cobalt, iron, boron, and silica, iron, cobalt, boron, and fluoride, and the like. These and other materials are descried in a book by J. Douglas Adam et al. entitled "Handbook of Thin Film Devices" (Academic Press, San Diego, Calif., 2000). Chapter 5 of this book beginning at page 185, describes "magnetic films for planar inductive components and devices;" and Tables 5.1 and 5.2 in his chapter describe many magnetic materials.

Figure 5:
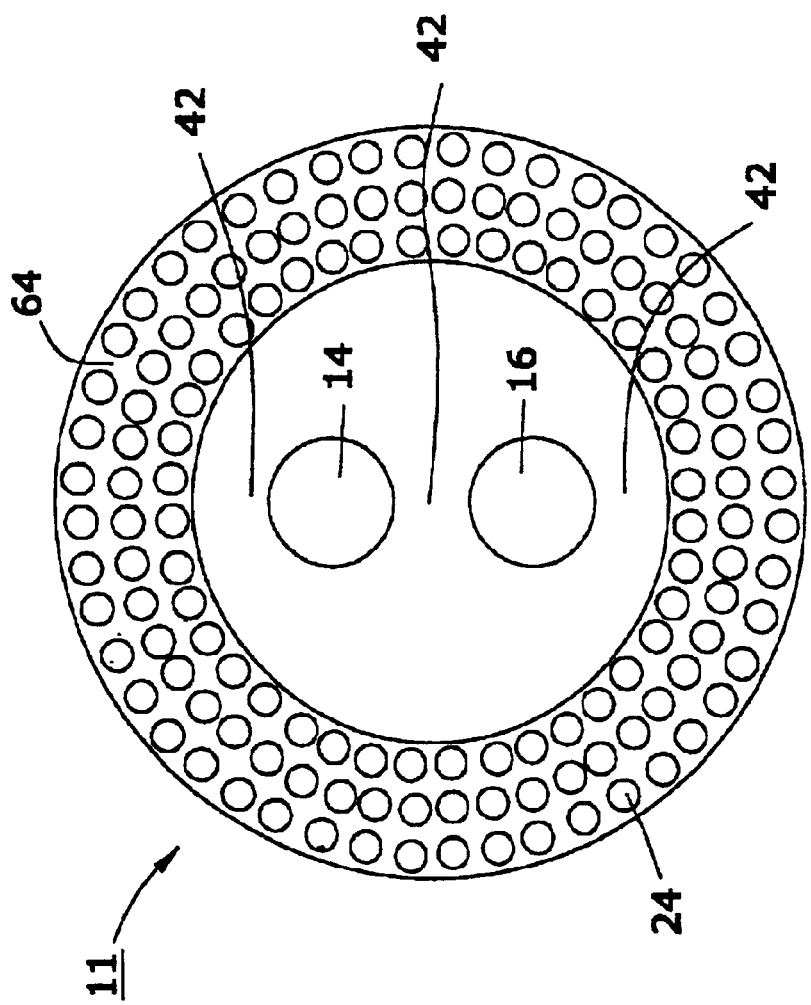
FIG. 5 is a sectional view of the shielded conductor assembly of FIG. 4.

FIG. 5 is a sectional view of the assembly 11 of FIG. 2. The device of FIG. 5, and of the other Figures of this application, is substantially flexible. As used in this specification, the term flexible refers to an assembly that can be bent to form a circle with a radius of less than 2 centimeters without breaking. Put another way, the bend radius of the coated assembly 11 can be less than 2 centimeters. Reference may be had, e.g., to U.S. Pat. Nos. 4,705,353, 5,946,439, 5,315,365, 4,641,917, 5,913,005, and the like. The entire disclosure of each of these United States patents is hereby incorporated by reference into this specification.

As will be apparent, even when the magnetic insulating properties of the assembly of this invention are not 100 percent effective, the assembly still prevents the rapid dissipation of heat to bodily tissue.

It is to be understood that the aforementioned description is illustrative only and that changes can be made in the apparatus, in the ingredients and their proportions, and in the sequence of combinations and process steps, as well as in other aspects of the invention Discussed herein, without departing from the scope of the invention as defined in the following claims.

Thus, e.g., although the process of this invention has been illustrated with regard to two separate, non-contiguous conductors 14 and 16, such process will also function with two contiguous conductors.

Devices Incorporating the Shielded Conductor Assembly

In this section of the specification, various devices that incorporate the shielded conductor assembly are described.

The invention described in this section of the specification relates generally to an implantable device that is immune or hardened to electromagnetic insult or interference. More particularly, this is directed to implantable medical leads that utilize shielding to harden or make these systems immune from electromagnetic insult, namely magnetic-resonance imaging insult.

Magnetic resonance imaging ("MRI") has been developed as an imaging technique to obtain images of anatomical features of human patients as well as some aspects of the functional activities of biological tissue; reference may be had, e.g., to John D. Enderle's "Introduction to Biomedical Engineering," Academic Press, San Diego, Calif., 2000 and, in particular, pages 783–841 thereof; reference may also be had to Joseph D. Bronzino's "The Biomedical Engineering Handbook," CRC Press, Boca Raton, Fla., 1995, and in particular pages 1006–1045 thereof. These images have medical diagnostic value in determining the state of the health of the tissue examined.

In an MRI process, a patient is typically aligned to place the portion of the patient's anatomy to be examined in the imaging volume of the MRI apparatus. Such an MRI apparatus typically comprises a primary magnet for supplying a constant magnetic field, $B_0$, which is typically 0.5 to 8.0 Tesla, and by convention, is along the z-axis and is substantially homogeneous over the imaging volume, and secondary magnets that can provide linear magnetic field gradients along each of three principal Cartesian axes in space (generally x, y, and z, or $x_1$, $x_2$ and $x_3$, respectively). A magnetic field gradient ($\Delta B_0/\Delta x_i$) refers to the variation of the field along the direction parallel to $B_0$ with respect to each of the three principal Cartesian axes, $x_i$. The apparatus also comprises one or more radio frequency (RF) coils which provide excitation and detection of the MRI signal. The RF excitation signal is an electromagnetic wave with an electrical field E and magnetic field $B_1$, and is typically transmitted at frequencies of 3–100 MHz.

The use of the MRI process with patients who have implanted medical assist devices, such as cardiac assist devices or implanted insulin pumps, often presents problems. As is known to those skilled in the art, implantable devices such as implantable pulse generators (IPGs), cardioverter/defibrillator/pacemakers (CDPs), and insulin pumps (IPs), are sensitive to a variety of forms of electromagnetic interference (EMI), because the enumerated devices include sensing and logic and control systems that respond to low-level electrical signals emanating from the monitored tissue region of the patient. Since the sensing systems and logic and control elements of these implantable devices are responsive to changes in local electromagnetic fields, the implanted devices are vulnerable to external sources of electromagnetic noise. In particular, the conductive leads used to connect the IPG, CDP, IP, or other medical devices to the tissues being stimulated and/or sensed, interact with the time-varying RF magnetic field ($B_1$), which are emitted during the magnetic resonance imaging (MRI) procedure, to generate electrical currents and electrical voltages in the implanted devices and leads, which can damage the medical device, or result in heating of the lead which in turn can harm the patient. Thus, patients with implantable devices are generally advised not to undergo magnetic resonance imaging (MRI) procedures.

To more appreciate the problem, the use of implantable cardiac assist devices during a MRI process will be briefly discussed.

The human heart may suffer from two classes of rhythmic disorders or arrhythmias: bradycardia and tachyarrhythmia. Bradycardia occurs when the heart beats too slowly, and may be treated by a common implantable pacemaker delivering low voltage (about 3 V) pacing pulses.

The common implantable pacemaker is usually contained within a hermetically sealed enclosure, in order to protect the operational components of the device from the harsh environment of the body, as well as to protect the body from the device. The common implantable pacemaker operates in conjunction with one or more electrically conductive leads, adapted to conduct electrical stimulating pulses to sites within the patient's heart, and to communicate sensed signals from those sites back to the implanted device. Furthermore, the common implantable pacemaker typically has a metal case and a connector block mounted to the metal case that includes receptacles for the electrically conductive leads which may be used for electrical stimulation or which may be used for sensing physiological signals. The battery and the circuitry associated with the common implantable pacemaker are hermetically sealed within the case. Electrical interfaces are employed to connect the electrically conductive leads outside the metal case with the medical device circuitry and the battery inside the metal case. Electrical interfaces serve the purpose of providing an electrical circuit path extending from the interior of a hermetically sealed metal case to an external point outside the case while maintaining the hermetic seal of the case. A conductive path is provided through the interface by a conductive pin that is electrically insulated from the case itself. Such interfaces typically include a ferrule that permits attachment of the interface to the case, the conductive pin, and a hermetic glass or ceramic seal that supports the pin within the ferrule and isolates the pin from the metal case.

A common implantable pacemaker can, under some circumstances, be susceptible to electrical interference such that the desired functionality of the pacemaker is impaired. For example, common implantable pacemaker requires protection against electrical interference from electromagnetic interference (EMI), defibrillation pulses, electrostatic discharge, or other generally large voltages or currents generated by other devices external to the medical device. As noted above, more recently, it has become crucial that cardiac assist systems be protected from magnetic-resonance imaging sources.

Such electrical interference can damage the circuitry of the cardiac assist systems or cause interference in the proper operation or functionality of the cardiac assist systems. For example, damage may occur due to high voltages or excessive currents introduced into the cardiac assist system, particularly voltages or currents induced in the electrically conductive leads, which can act as antennas and pick up externally induced electromagnetic fields, particularly the time-varying RF magnetic field.

Therefore, it is required that such voltages and currents be limited at the input of such cardiac assist systems, e.g., at the interface of the electrically conductive lead and the medical device. Protection from such voltages and currents has typically been provided at the input of a cardiac assist system by the use of one or more zener diodes and one or more filter capacitors. For example, one or more zener diodes may be connected between the circuitry to be protected, e.g., pacemaker circuitry, and the metal case of the medical device in a manner which grounds voltage surges and current surges through the diode(s). Such zener diodes and capacitors used for such applications may be in the form of discrete components mounted relative to circuitry at the input of a connector block where various leads are connected to the implantable medical device, e.g., at the interfaces for such leads.

However, such protection, provided by zener diodes and capacitors placed at the input of the medical device, increases the congestion of the medical device circuits, at least one zener diode and one capacitor per input/output connection or interface. This is contrary to the desire for increased miniaturization of implantable medical devices. Further, when such protection is provided, interconnect wire length for connecting such protection circuitry and pins of the interfaces to the medical device circuitry that performs desired functions for the medical device tends to be undesirably long. The excessive wire length may lead to signal loss and undesirable inductive effects. The wire length can also act as an antenna that conducts undesirable electrical interference signals to sensitive CMOS circuits within the medical device to be protected.

Despite the protection provided to the implanted medical device, RF energy presents other risks to the patient:

RF energy that is inductively coupled into the electrically conductive lead causes intense heating along the length of the wire, and at the electrodes that are attached to the heart wall. This heating may be sufficient to ablate the interior surface of the blood vessel through which the wire lead is placed, and may be sufficient to cause scarring at the point where the electrodes contact the heart A further result of this ablation and scarring is that the sensitive node that the electrode is intended to pace with low voltage signals becomes desensitized, so that pacing the patient's heart becomes less reliable, and in some cases fails altogether.

Additionally, RF energy that is inductively coupled into the electrically conductive lead can induce voltages within the lead and at the electrode there are large (50 to 100 volts) relative to cardiac pacing voltages (1–5 volts). These very signals can inappropriately pace the heart or other stimulated organ or tissue. Inappropriate stimulation of the heart can result in rhythmic disorders or arrhythmias that include bradycardia and tachyarrhythmia.

Another conventional solution for protecting the implantable medical device from electromagnetic interference is disclosed in FIG. 1 of U.S. Pat. No. 5,549,642, the entire disclosure of which is hereby incorporated by reference into this specification. in illustrated in FIG. 1. Referring to such FIG. 1, it will be seen that such FIG. 1 is a schematic view of an implantable medical device 10 embodying protection against electrical interference. At least one lead 16 is connected to the implantable medical device 10 in a connector block region using an interface.

In the case where implantable medical device 10 is a pacemaker implanted in a body, the pacemaker 10 includes at least one or both of pacing and sensing leads represented generally as leads 15,16 to sense electrical signals attendant to the depolarization and repolarization of the heart, and to provide pacing pulses for causing depolarization of cardiac tissue in the vicinity of the distal ends thereof.

In a typical circuit (not shown) that is used conventionally to protect from electromagnetic interference, protection circuitry is usually provided using a diode array component. A diode array often consists of five Zener diodes triggered semiconductor controlled rectifiers (SCRs) with anti-parallel diodes arranged in an array with one common connection. This allows for a small footprint despite the large currents that may be carried through the device during defibrillation, e.g., 10 amps. Silicon controlled rectifiers turn on and limit the voltage across the device when excessive voltage and current surges occur.

In this prior art embodiment, each of the Zener diode triggered silicon controlled rectifiers is connected to an electrically conductive pin. Further, each electrically conductive pin is connected to a medical device contact region to be wire bonded to pads of a printed circuit board. The diode array component is connected to the electrically conductive pins via the die contact regions along with other electrical conductive traces of the printed circuit board.

Other attempts have been made to protect implantable devices from MRI fields. For example, U.S. Pat. No. 5,968,083 (to Ciciarelli et al.) describes a device adapted to switch between low and high impedance modes of operation in response to EMI insult. Furthermore, U.S. Pat. No. 6,188,926 (to Vock) discloses a control unit for adjusting a cardiac pacing rate of a pacing unit to an interference backup rate when heart activity cannot be sensed due to EMI.

Although, conventional medical devices provide some means for protection against electromagnetic interference, these conventional devices require much circuitry and fail to provide fail-safe protection against radiation produced by magnetic-resonance imaging procedures. Moreover, the conventional devices fail to address the possible damage that can be done at the tissue interface due to RF-induced heating, and they fail to address the unwanted heart stimulation that may result from RF-induced electrical currents.

Additionally, implanted medical assist devices can degrade the quality of the image obtained by the MRI process. As is known to those skilled in the art, signal loss and disruption of a magnetic resonance image can be caused by disruption of the local magnetic field, which perturbs the relationship between position and image, which are crucial for proper image reconstruction. More specifically, the spatial encoding of the MRI signal provided by the linear magnetic field can be disrupted, making image reconstruction difficult or impossible. The relative amount of artifact seen on an MRI image due to signal disruption is dependent upon such factors as the magnetic susceptibility of the materials used in the medical device, as well as the shape, orientation, and position of the medical device within the body.

All non-permanently magnetized materials have non-zero magnetic susceptibilities and are to some extent magnetic. Materials with positive magnetic susceptibilities<approximately 0.01 are referred to as paramagnetic are not overly responsive to an applied magnetic field, and are often considered as non-magnetic. Materials with magnetic susceptibilities>0.01 are referred to as ferromagnetic. These materials can respond very strongly to an applied magnetic field, and are also referred to as soft magnets, as there properties do not manifest until exposed to an external magnetic field.

Paramagnetic materials (e.g. titanium), are frequently used to encapsulate and shield and protect the sensitive internal electrical components used in implanted medical devices due to their low magnetic susceptibility. These enclosures operate by deflecting electromagnetic fields. However, although paramagnetic materials are less susceptible to magnetization than ferromagnetic objects, they can also produce image artifacts due to eddy currents generated in the implanted medical devices by externally applied electromagnetic fields, such as the RF fields used in MRI procedures. These eddy currents produce localized magnetic fields which disrupt and distort the magnetic resonance image. Furthermore, the medical device and lead shape, orientation, and position within the body make it difficult to control image distortion due to eddy currents induced by the RF fields used in MRI procedures.

Thus, it is desirable to provide protection against electromagnetic interference, without requiring much circuitry, and to provide fail-safe protection against radiation produced by magnetic-resonance imaging procedures. Moreover, it is desirable to provide devices that prevent the possible damage that can be done at the tissue interface due to induced electrical signals and due to thermal tissue damage. Furthermore, it is desirable to provide to provide an effective means for transferring energy from one point in the body to another point without having the energy causing a detrimental effect upon the body.

In accordance with this embodiment of the invention there is provided a magnetically shielded medical device and lead, wherein said magnetic shield consists of a nanomagnetic particulate material.

A coating of nanoparticles that consists of a mixture of aluminum oxide (AlO3), iron, and other particles has the ability to deflect electromagnetic fields, while remaining electrically non-conductive. Preferably the particle size in such a coating is approximately 10 nanometers. Preferably the particle packing density is relatively low so as to minimize electrical conductivity. Such a coating placed on a metallic object (such as an implantable pacemaker or pacemaker lead) is capable of deflecting electromagnetic fields, thereby protecting sensitive internal components, while also preventing the formation of eddy currents in the metallic object or coating. The absence of eddy currents in a metallic medical device and/or lead provides several advantages: (1)reduction or elimination of heating, (2) reduction or elimination of electrical voltages which can damage the device and/or inappropriately stimulate internal tissues and organs, and (3) reduction or elimination of disruption and distortion of a magnetic resonance image.

Figure 6A:
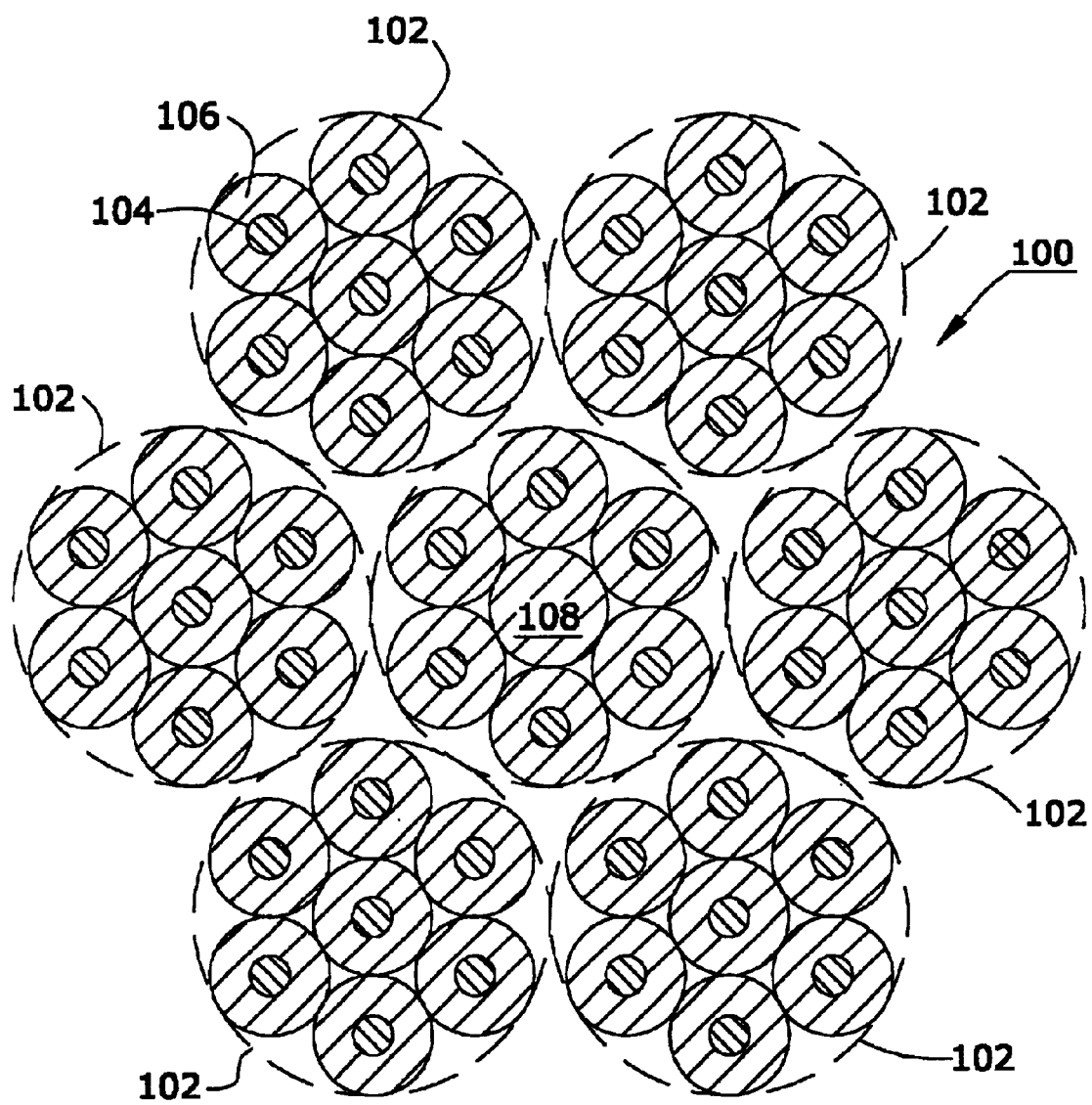
FIG. 6 is a schematic of a directly coated single and multiple strand, and a single and multiple conductor leads.
Figure 6B:
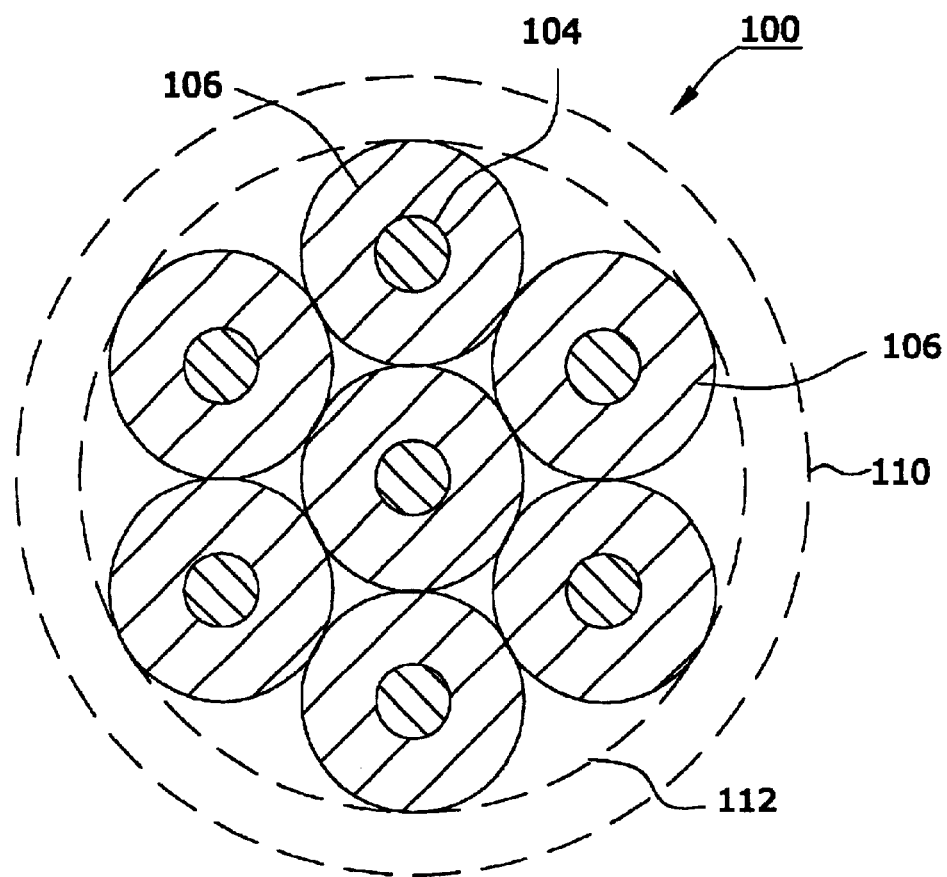
Figure 6C:
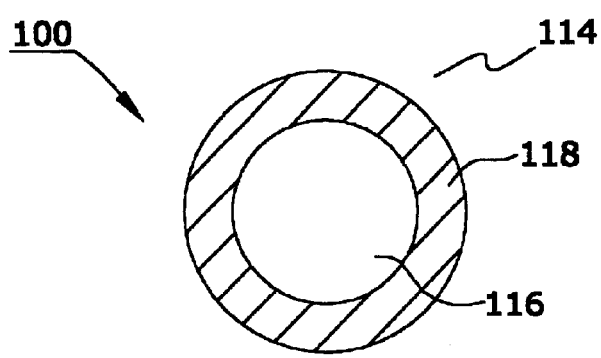

FIGS. 6A, 6B, and 6C are schematics of an electrical conductor assembly 100 to which a nanomagnetic coating is applied directly to the surface of the electrical conductor used in an implanted lead. Referring to FIG. 6A, it will be seen that seven subsassemblies 102 comprise the conductor assembly 100. Each subsassembly 102 is comprised of 7 single strands 104 of conductors coated with nanomagnetic particles 106. The assembly 100 also preferably comprises a centrally disposed conductor 108 that may be used to provide mechanical integrity and/or may be used to conduct electricity.

FIG. 6B is a schematic view of a single strand 110 comprised of a multiplicity of coated strands 104 coated with nanomagnetic particles 106. The entire assembly is preferably enclosed within a biocompatible sheath 112. In the preferred embodiment depicted, the sheath 112 is coated with nanomagnetic particles 106.

FIG. 6C is a sectional view of a single strand 114 that comprises a single conductor 116 coated with nanomagnetic material 118.

As will be apparent from FIGS. 6A, 6B, and 6C, the lead can be a single strand conductor or multiple strand conductor, and the lead may consist of a single conductor or multiple conductors. It is to be understood that multiple strand conductors may be shielded by coating each strand separately, or by coating the multiple strand bundle. It is also to be understood that the multiple conductors within a single lead may be positioned concentrically to one another, or positioned spaced apart. It is also to be understood that the internally positioned conductors may be free to move, for example to rotate or translate, to for example control the motion of an active fixation electrode. By way of illustration, the shielded conductors described in FIGS. 6A and/or 6B and/or 6C may be used in the lead designs shown in U.S. Pat. Nos. 6,289,251, 6,285,910, 6,192,280, 6,185, 463, 6,178,355, 6,144,882, 6,119,042, 6,096,069, 6,066,166, 6,061,598, 6,040,369, 6,038,463, 6,026,567, 6,018,683, 6,016,436, 6,006,122, 5,999,858, 5,991,668, 5,968,087, 5,968,086, 5,967,977, 5,964,795, 5,957,970, 5,957,967, 5,957,965, 5,954,759, 5,948,015, 5,935,159, 5,897,585, 5,871,530, 5,871,528, 5,853,652, 5,796,044, 5,760,341, 5,702,437, 5,676,694, 5,584,873, 5,522,875, 5,423,881, 5,411,545, 5,354,327, 5,336,254, 5,336,253, 5,324,321, 5,303,704, 5,238,006, 5,217,027, and 5,007,435, the entire disclosure of which is hereby incorporated by reference into this specification. As will be apparent, such modified devices all contain nanomagnetic coatings which shield the assemblies from electromagnetic radiation.

Figure 7A:
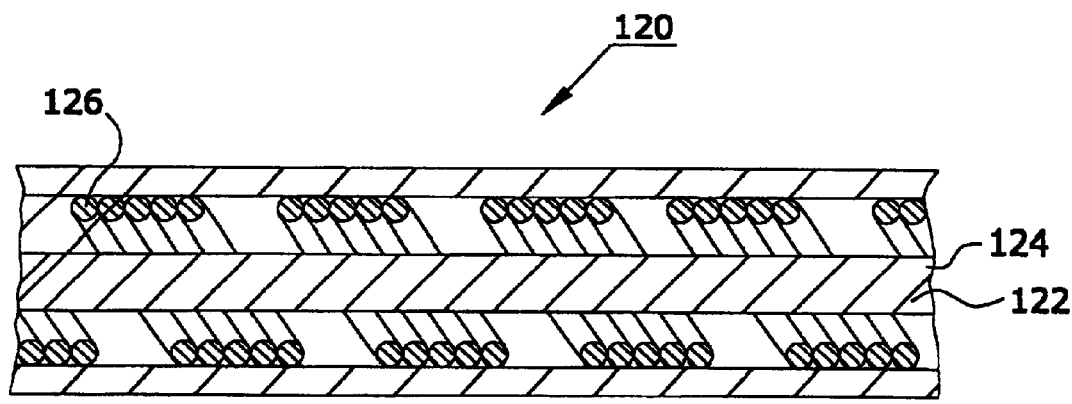
FIG. 7 is a schematic or a straight or a coiled shielded conductor(s)

FIG. 7A is a schematic of shielded conductor assembly 120 comprised of a single conductor 122 coated with nanomagnetic material 124; the conductor 122 is a straight conductor. The conductor assembly 120 also is comprised of a multifilar coiled conductor 126 with a spiral configuration; reference to such a multifilar conductor is made, e.g., in U.S. Pat. No. 5,954,759, the entire disclosure of which is hereby incorporated by reference into this specification.

Figure 7B:
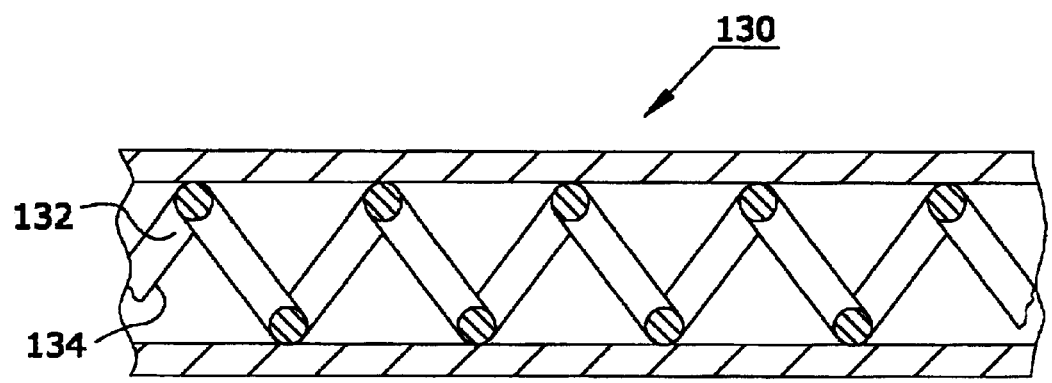

FIG. 7B is a schematic of a shielded conductor assembly 130 comprised of a monofilar coiled conductor 132 coated with nanomagnetic particles 134; such monofilar coiled conductor assemblies are disclosed, e.g., in U.S. Pat. No. 5,954,759. As will be apparent, the coated nanomagnetic particle assembly of this FIG. 7B is resistant to electromagnetic radiation, forming a protective sheath around the core conductor 132.

With reference to FIGS. 7A and 7B, it is to be understood that the conductors used in either the straight conductor or coiled conductor embodiments may be either single strand or multiple strand. Multiple strand conductors may be shielded by coating each strand separately, or by coating the multiple strand bundle. Straight conductors or coiled conductors can also be used to apply torque or axial loads. By way of illustration, the shielded conductors described in FIGS. 7A and/or 7B may be used in the lead designs shown in U.S. Pat. Nos. 6,289,251, 6,285,910, 6,192,280, 6,185,463, 6,178,355, 6,144,882, 6,119,042, 6,096,069, 6,066,166, 6,061,598, 6,040,369, 6,038,463, 6,026,567, 6,018,683, 6,016,436, 6,006,122, 5,999,858, 5,991,668, 5,968,087, 5,968,086, 5,967,977, 5,964,795, 5,957,970, 5,957,967, 5,957,965, 5,954,759, 5,948,015, 5,935,159, 5,897,585, 5,871,530, 5,871,528, 5,853,652, 5,796,044, 5,760,341, 5,702,437, 5,676,694, 5,584,873, 5,522,875, 5,423,881, 5,411,545, 5,354,327, 5,336,254, 5,336,253, 5,324,321, 5,303,704, 5,238,006, 5,217,027, and 5,007,435, the entire disclosure of which is hereby incorporated by reference into this specification. When so used, the modified assemblies thus produced are resistant to electromagnetic radiation.

Figure 8A:
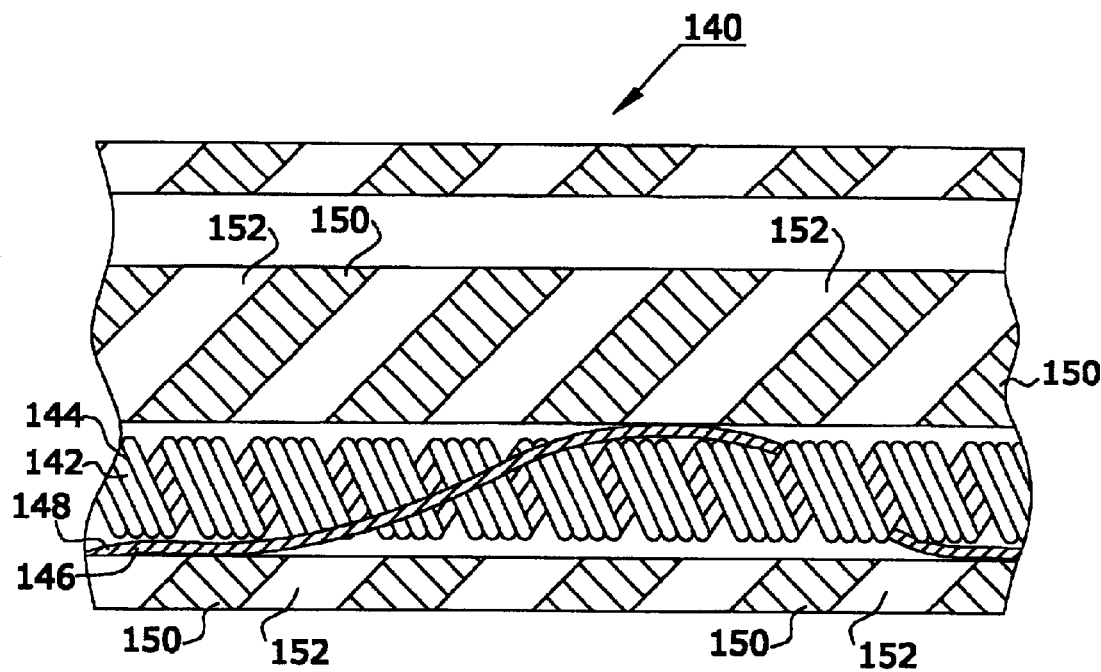
FIG. 8 is a schematic of discontinuous coated shielding.

FIG. 8A is a schematic of a shielded conductor assembly 140 comprised of a multifilar conductor 142 coated with nanomagnetic particles 144, and a monofilar conductor 146 coated with nanomagnetic particles 148. In the embodiment depicted in FIG. 8A, the monofilar conductor 146 is disposed outside of the multifilar conductor 142.

Referring again to FIG. 8A, and in one embodiment, only a portion of the conductors 142 and/or 146 are shielded. Thus, in the embodiment depicted in FIG. 8A, is section 150 these conductors are shielded, whereas in section 152 these conductors are not shielded.

In another embodiment, not shown, the dicontinuous shield is produced by a discontinuous coating of nanomagnetic particles. This coating, e.g., may be may be intermittingly discontinuous along its axial dimension, to provide for example, reduced exposure to an externally applied electromagnetic field. This coating may be, e.g., discontinuous at its proximal end, to provide for example, an electrically conductive surface for attachment to a medical device, such as an implantable pulse generator, a cardioversion-defibrilator pacemaker, an insulin pump, or other tissue or organ stimulating or sensing device. This coating, e.g., may be discontinuous along its distal end, to provide for example, an electrically conductive surface for contacting tissues or organs.

Figure 8B:
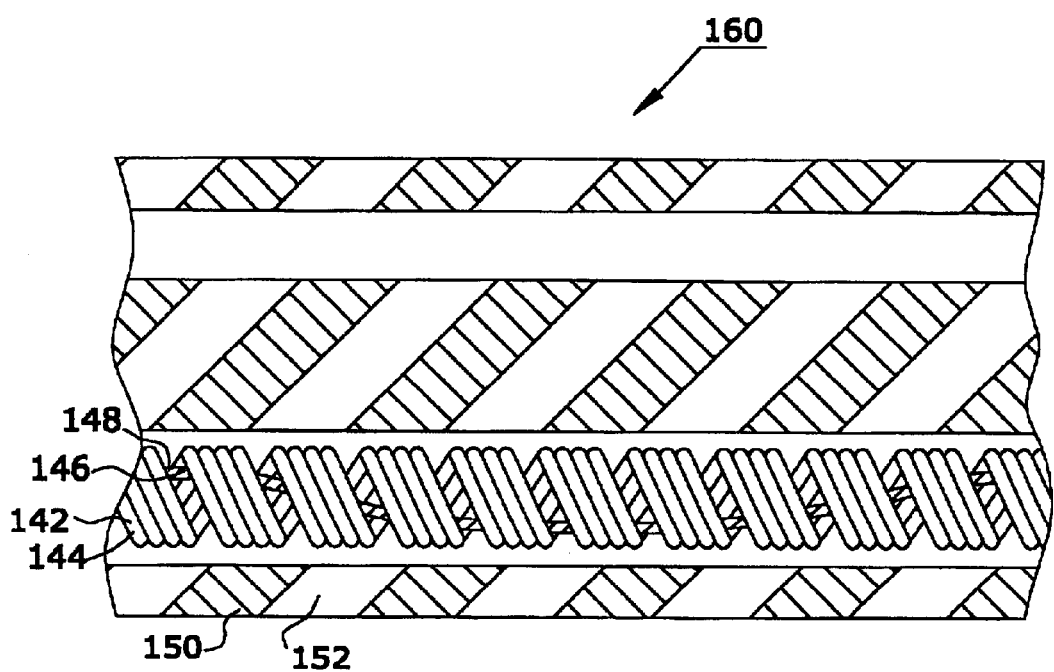

FIG. 8B is a sectional view of a conductor assembly 160 that is similar to the assembly disclosed in FIG. 8A but differs therefrom in that the monofilar conductor 146 is disposed inside the multifilar conductor 142.

Figure 8C:
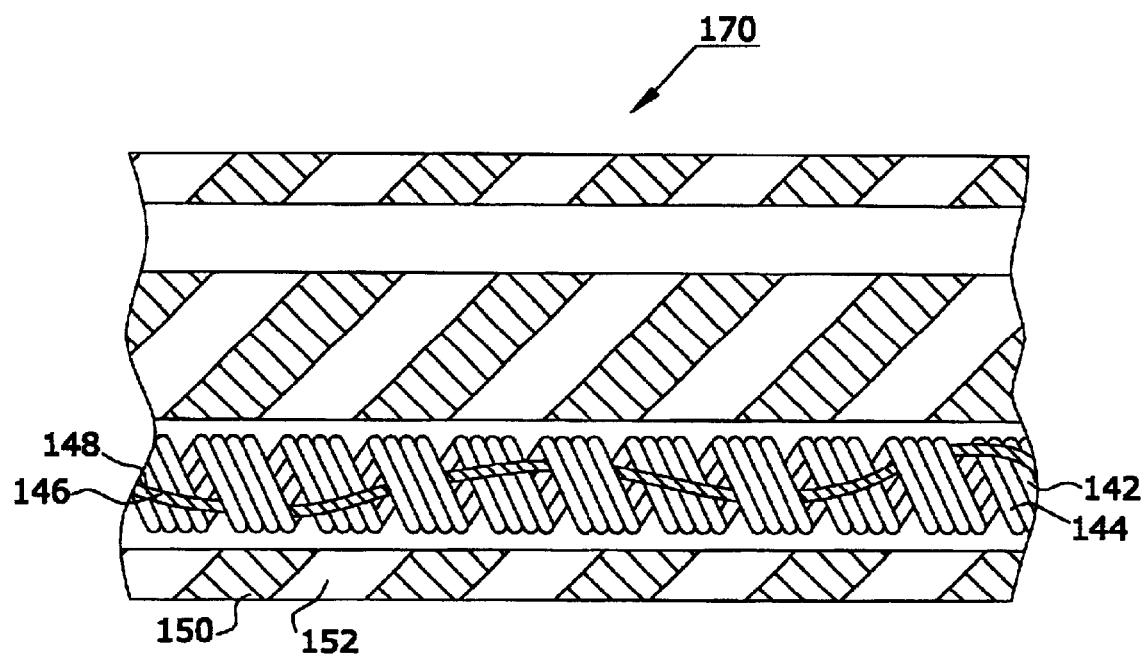

FIG. 8C is a sectional view of a conductor assembly 170 that is similar to the assemblies disclosed in FIGS. 8A and 8B but differs therefrom in that the monofilar conductor 146 is partially disposed outside of the multifilar conductor 142, and partially disposed within the multifilar conductor 142.

A discontinuous shield may be applied to non-wire conductors, such as for example a solid rod or other geometry conductor, used for example as an electrode for transmitting and/or receiving electrical signals to/from tissues or organs. The discontinuous shield may be applied to any of the conductor or lead configurations described above. By way of illustration, the shielded conductors described in FIGS. 8A, 8B, and 8C may be used in the lead designs shown in U.S. Pat. Nos. 6,289,251, 6,285,910, 6,192,280, 6,185,463, 6,178,355, 6,144,882, 6,119,042, 6,096,069, 6,066,166, 6,061,598, 6,040,369, 6,038,463, 6,026,567, 6,018,683, 6,016,436, 6,006,122, 5,999,858, 5,991,668, 5,968,087, 5,968,086, 5,967,977, 5,964,795, 5,957,970, 5,957,967, 5,957,965, 5,954,759, 5,948,015, 5,935,159, 5,897,585, 5,871,530, 5,871,528, 5,853,652, 5,796,044, 5,760,341, 5,702,437, 5,676,694, 5,584,873, 5,522,875, 5,423,881, 5,411,545, 5,354,327, 5,336,254, 5,336,253, 5,324,321, 5,303,704, 5,238,006, 5,217,027, and 5,007,435, the entire disclosure of which is hereby incorporated by reference into this specification. Because these devices are coated with nanomagnetic particles, they are resistant to electromagnetic radiation.

Figure 9A:
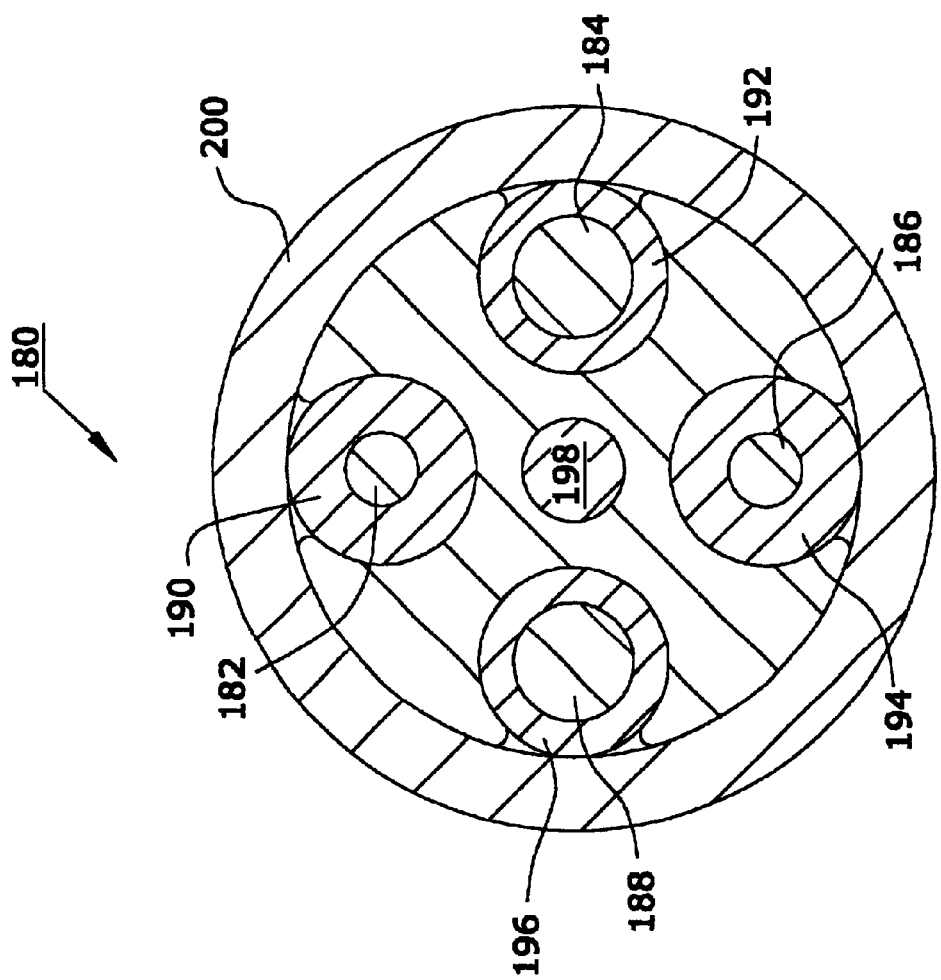
FIG. 9 is a schematic of multiple discontinuously shielded conductors.

FIG. 9A is a sectional view of a multiple discontinuously shielded conductor assembly 180 that is comprised of a multiplicity of shielded conductors 182, 184, 186, and 188, each of which is coated discontinuously or continuously with nanomagnetic shielding 190, 192, 194, and 196. The centrally disposed conductor 198 is preferably a pacing lead, and the shielded conductors 182, 184, 186, and 188 are preferably cardioversion defibrillation leads. In the embodiment depicted, the entire assembly 180 is shielded with a layer of nanomagnetic material 200. As will be apparent, the use of discontinuous coating enables the multiple conductors to make electrical contact at one or more points along their axial dimension, to provide redundant electrical channels, in the event one channel should break. The discontinuous coating provides reduced exposure to externally applied electromagnetic fields. The discontinuous shield may be; intermittingly discontinuous along its axial dimension, discontinuous at its proximal end, or discontinuous along its distal end. It is to be understood that the discontinuous shield may be applied to any of the conductor or lead configurations described above.

Figure 9B:
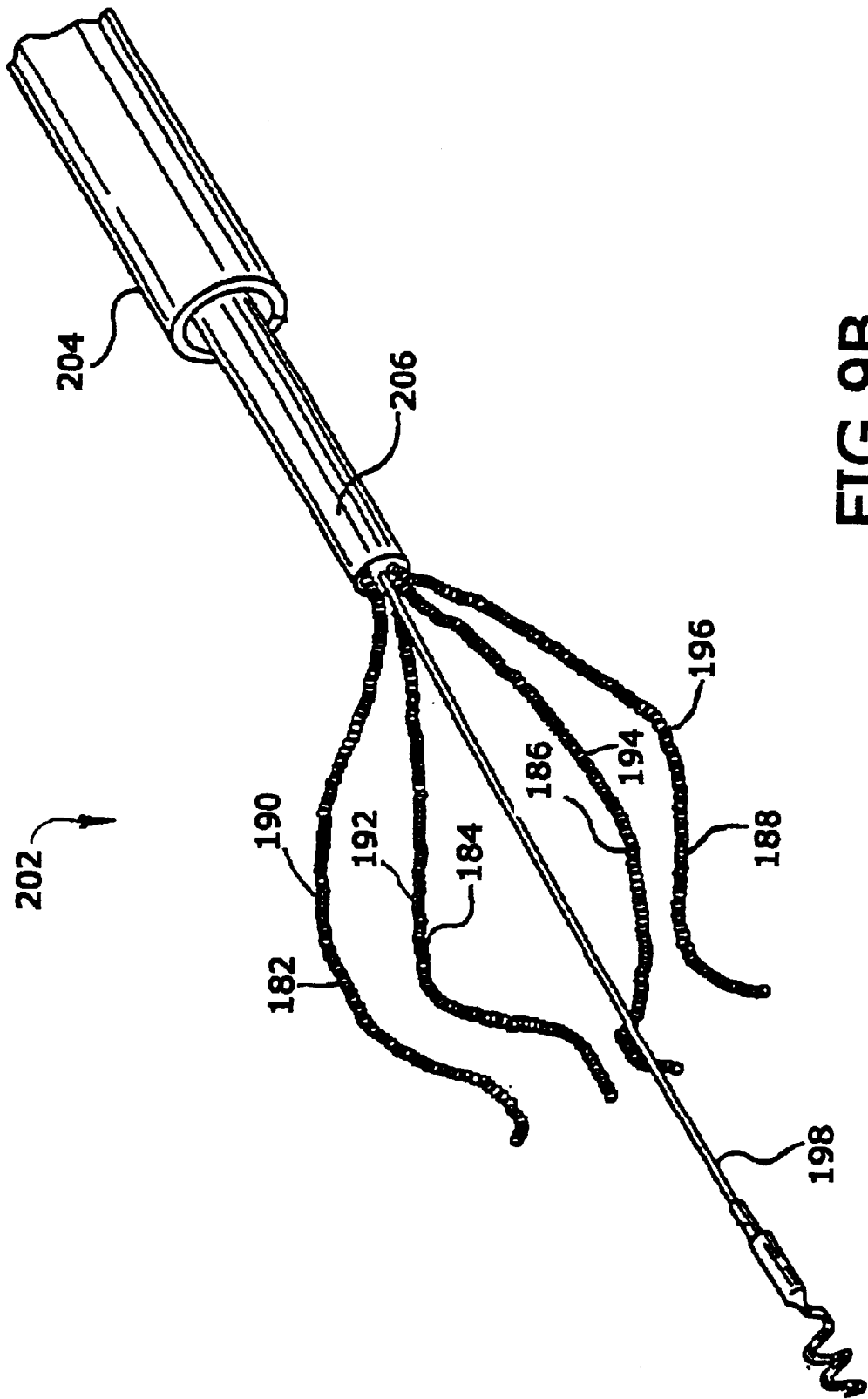

FIG. 9B is illustrates a multiconductor lead 202 connected to a catheter 204 and a sheath 206. This assembly is similar to the assembly depicted in U.S. Pat. No. 6,178,355, the entire disclosure of which is hereby incorporated by reference into this specification, but differs therefrom in that the use of nanomagnetic particle shielding provides resistance to electromagnetic radiation.

Thus, by way of further illustration, the shielded conductors described in FIGS. 9A and 9B may be used in the lead designs shown in U.S. Pat. Nos. 6,285,910, 6,178,355, 6,119,042, 6,061,598, 6,018,683, 5,968,086, 5,957,967, 5,954,759, 5,871,530, 5,676,694 numbers the entire disclosure of which is hereby incorporated by reference into this specification.

Figure 10:
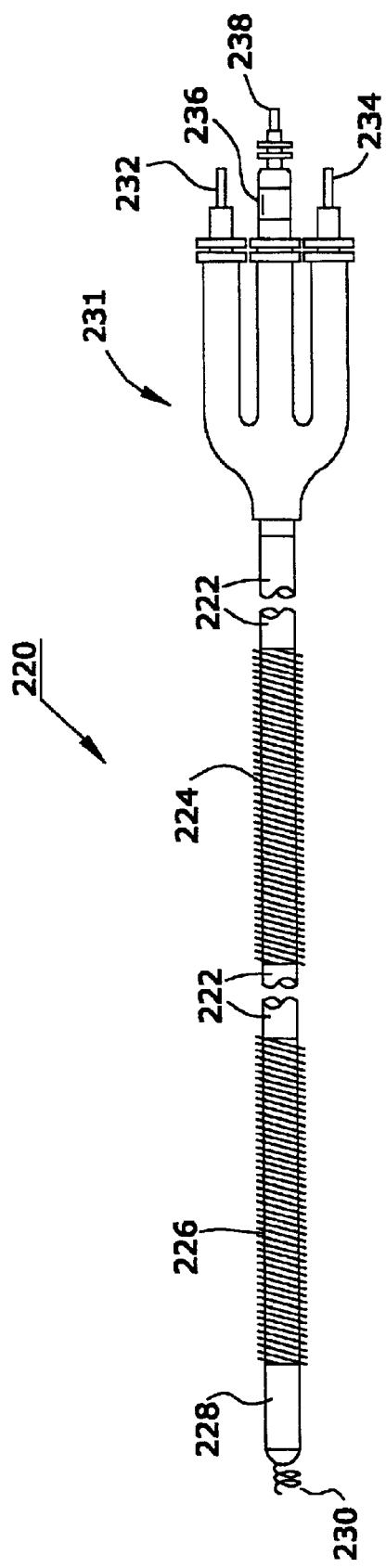
FIG. 10 is a schematic of a discontinuously shielded conductor positioned on the exterior surface of a lead.

FIG. 10 is a schematic of a discontinuously shielded conductor 220 similar to the assembly depicted in FIG. 1 of U.S. Pat. No. 6,016,436; the entire disclosure of such patent is hereby incorporated by reference into this specification.

As will be seen by reference to FIG. 10, the shielded conductor assembly 220 is positioned on the exterior surface 222 of a shielded conductor 224.

In one embodiment, the assembly 220 contains a continuous shielding 224. In another embodiment, the assembly 220 comprises both a shielded region 224 and a discontinuous unshielded region 226.

In one embodiment, the lead body carries at its distal end an insulative electrode head 228, which may be fabricated of a relatively rigid biocompatible plastic, such as a polyurethane, that carries an advanceable helical electrode 230. At its proximal end, the lead carries a trifurcated connector assembly 231 provided with two connector pins 232/234, each coupled to one of two elongated defibrillation electrode coils 224/226. Connector assembly 231 also carries an IS-1 compatible, in-line connector assembly provided with a connector ring 236 that is coupled to defibrillation electrode coil 226 and a connector pin 238 coupled to helical electrode 230.

In one embodiment, and referring again to FIG. 10, the coating is intermittingly discontinuous along its axial dimension, to enable for example direct stimulation and sensing of tissues and organs, while providing for example, reduced exposure to an externally applied electromagnetic field. By way of illustration, the shielded conductors described in FIG. 10 may be used in the lead designs shown in U.S. Pat. Nos. 6,289,251, 6,285,910, 6,119,042, 6,066,166, 6,061,598, 6,038,463, 6,018,683, 5,957,970, 5,957,967, 5,935,159, 5,871,530, 5,702,437, 5,676,694, 5,584,873, 5,336,254, 5,336,253, 5,238,006, 5,217,027, the entire disclosure of which is hereby incorporated by reference into this specification. The conductor assemblies so modified are resistant to electromagnetic radiation.

Figure 11:
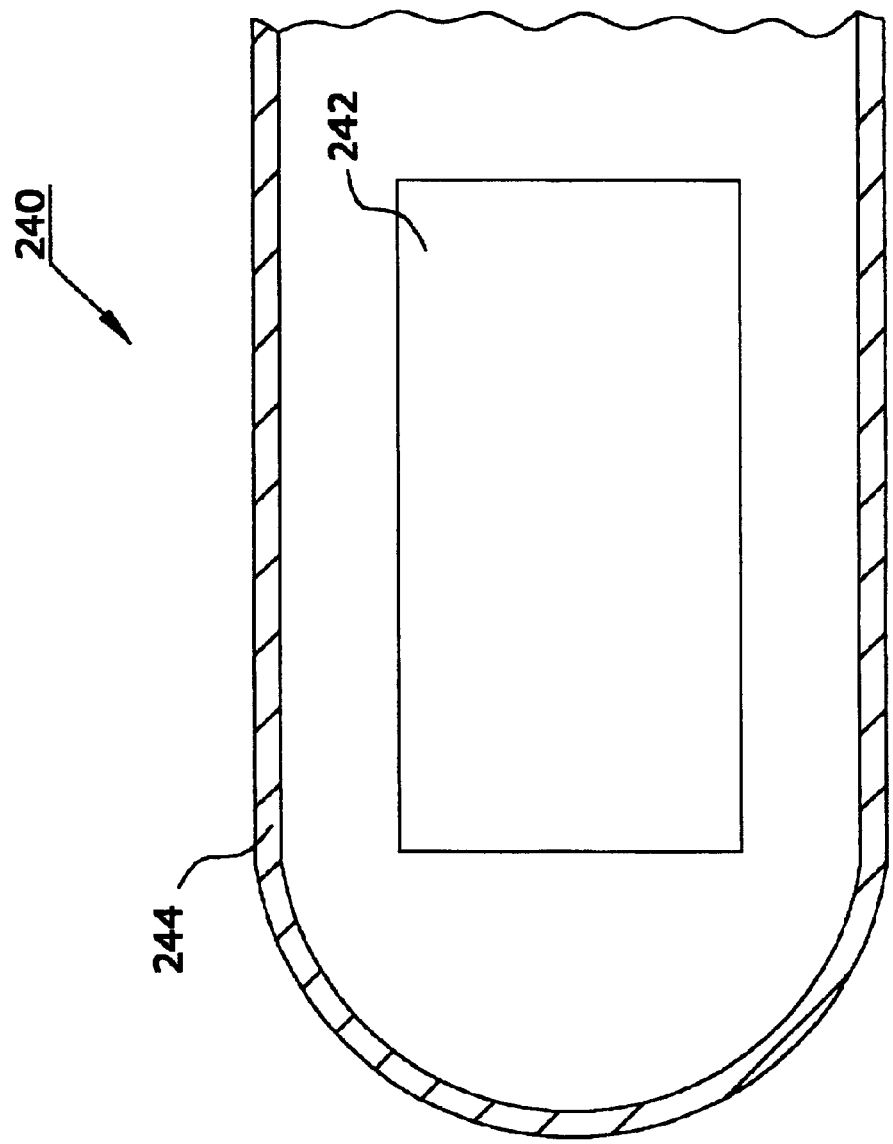
FIG. 11 is a schematic of nanomagnetic coating used to shield electrical components located within leads.

FIG. 11 is a partial schematic view of an shielded electrical assembly 240 comprised of electrical circuitry 242 disposed within nanomagnetic shield 244.

One may use nanomagnetic coating used to shield electronic components located within leads.

Figure 12A:
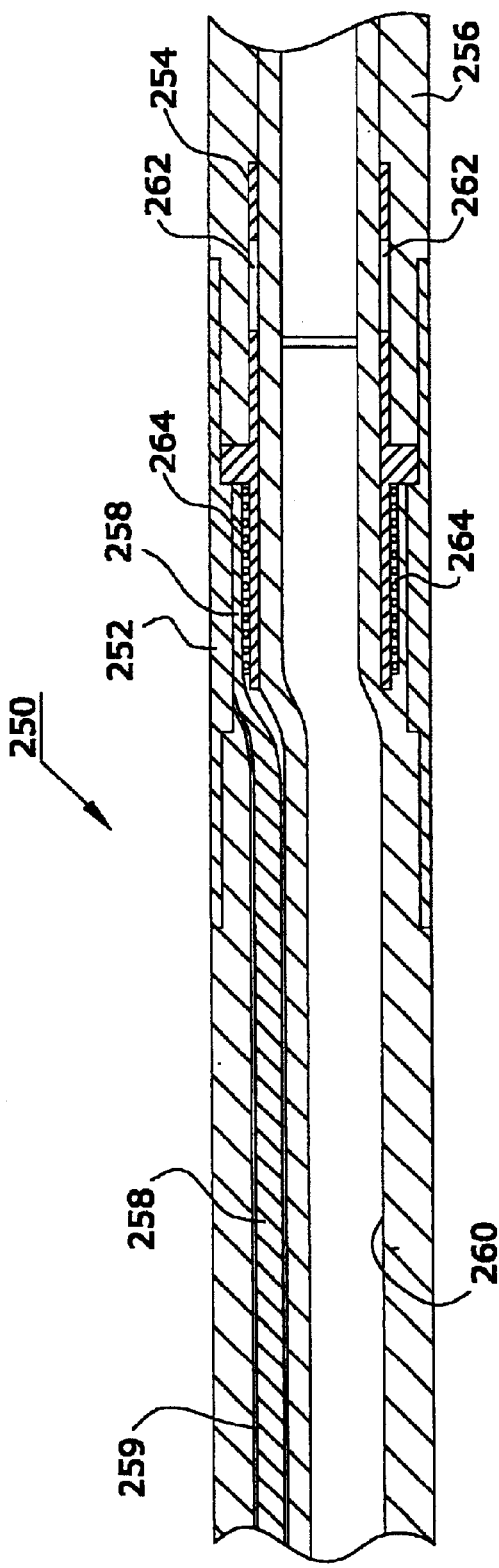
FIG. 12 is a schematic of nanomagnetic coating applied to lead components.

FIG. 12A is a schematic of a medical lead with stranded conductors 250 similar to that depicted in U.S. Pat. No. 6,026,567, the entire disclosure of which is hereby incorporated by reference into this specification. Referring to FIG. 12A, and in the preferred embodiment depicted therein, the assembly 250 is comprised of a ring electrode 252, a core 254, a distal insulative sleeve 256, a conductor 258, a lumen 260, cross bores 262, a distal portion 264, and a point 266 adjacent to a shoulder (not shown, but see FIGS. 2, 3, and 4 of U.S. Pat. No. 6,026,567).

Figure 12B:
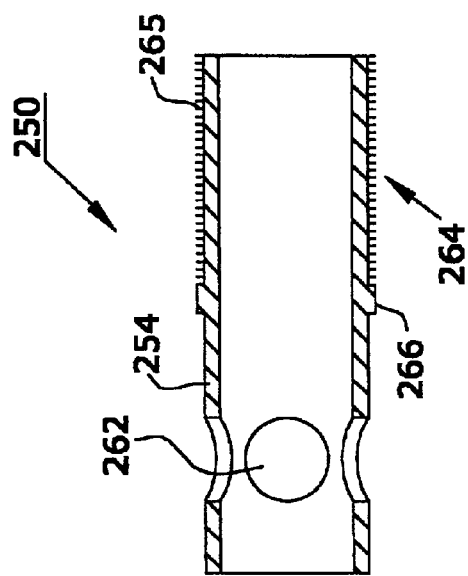

FIG. 12B is an enlarged sectional view of a portion of device 250.

Figure 12C:
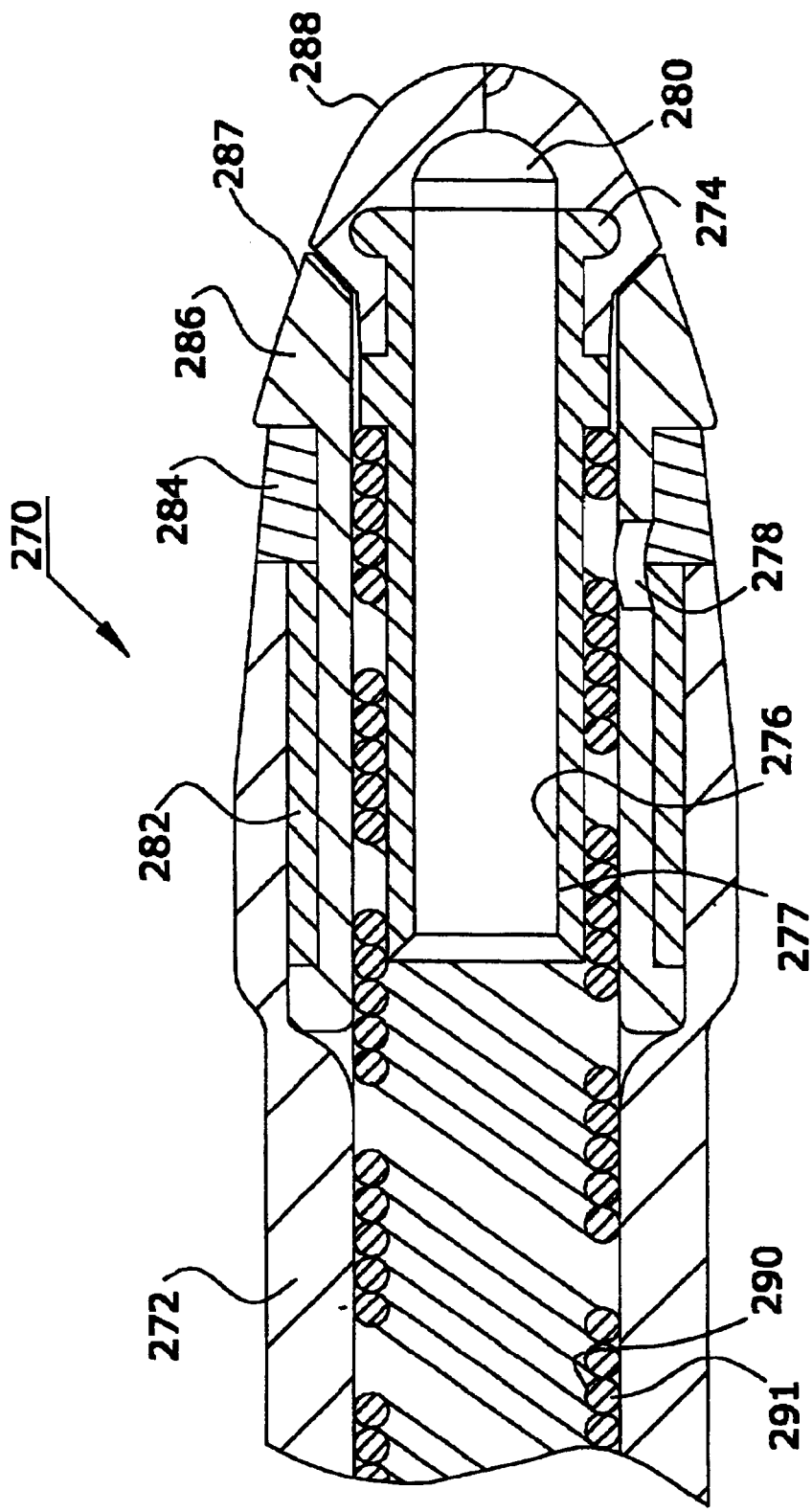

FIG. 12C is a partial sectional view of a lead 270 that is similar in configuration to the guidewire placed implantable lead with tip seal disclosed in U.S. Pat. No. 6,192,280 (the entire disclosure of which is hereby incorporated by reference into this specification) but differs therefrom in that it is comprised of nanomagnetic coating. Referring to FIG. 12C, the lead 270 is comprised of an elongated insulative lead body 272, a laterally extending ridge 274, an internal conductive sleeve 276, a bore 278, a cup-shaped seal member 280, a plastic band 282, a controlled release device 284, an electrode 286, a distal tip 288, and a coiled conductor 290. In the embodiment depicted, elements 276, 286, and 290 are each coated with nanomagnetic particles 277, 287, and 291, respectively. Alternatively, or additionally, other metal-containing portions of such assembly 270 (not shown) also may be coated with nanomagnetic particles.

Referring again to FIGS. 12A, 12B, and 12C, conductor 258 is coated with nanomagnetic coating 259, and core 264 is coated with nanomagnetic coating 265. As will be apparent, such nanomagnetic coating may be applied to miscellaneous components used to assemble leads and attach leads. By way of illustration, the shielded conductors described in FIGS. 12A, 12B, and 12C may be used in the lead designs shown in U.S. Pat. Nos. 6,289,251, 6,285,910, 6,192,280, 6,185,463, 6,178,355, 6,144,882, 6,119,042, 6,096,069, 6,066,166, 6,061,598, 6,040,369, 6,038,463, 6,026,567, 6,018,683, 6,016,436, 6,006,122, 5,999,858, 5,991,668, 5,968,087, 5,968,086, 5,967,977, 5,964,795, 5,957,970, 5,957,967, 5,957,965, 5,954,759, 5,948,015, 5,935,159, 5,897,585, 5,871,530, 5,871,528, 5,853,652, 5,796,044, 5,760,341, 5,702,437, 5,676,694, 5,584,873, 5,522,875, 5,423,881, 5,411,545, 5,354,327, 5,336,254, 5,336,253, 5,324,321, 5,303,704, 5,238,006, 5,217,027, and 5,007,435, the entire disclosure of which is hereby incorporated by reference into this specification.

Figure 13A:
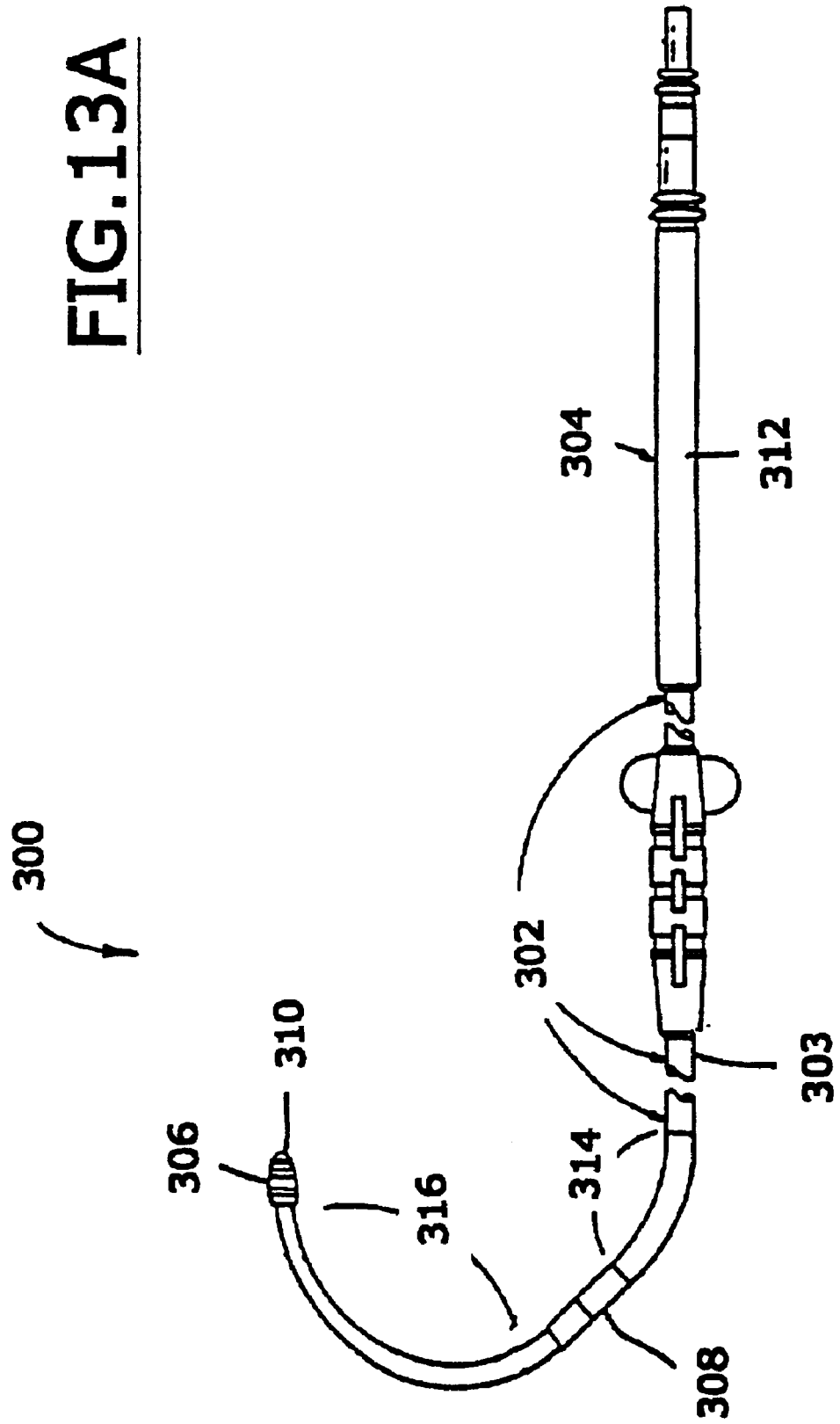
FIG. 13 is a schematic of nanomagnetic coating applied to mechanical members within a lead.

FIG. 13A is a schematic view of a catheter assembly 300 that is similar to the catheter assembly disclosed in U.S. Pat. No. 6,144,882, the entire disclosure of which is hereby incorporated by reference into this specification. Referring to FIG. 13A, it will be seen that assembly 300 is comprised of a elongated lead 302, a connector assembly 304, an electrode 306, a generally straight transition zone 308, a tip electrode 310, an anchoring sleeve 312, a first bent area 314, and a second bent area 316. In the embodiment depicted in FIG. 13A, elongated lead 302 and/or other conductive portions (not shown) may be coated with nanomagnetic particles 303.

Figure 13B:
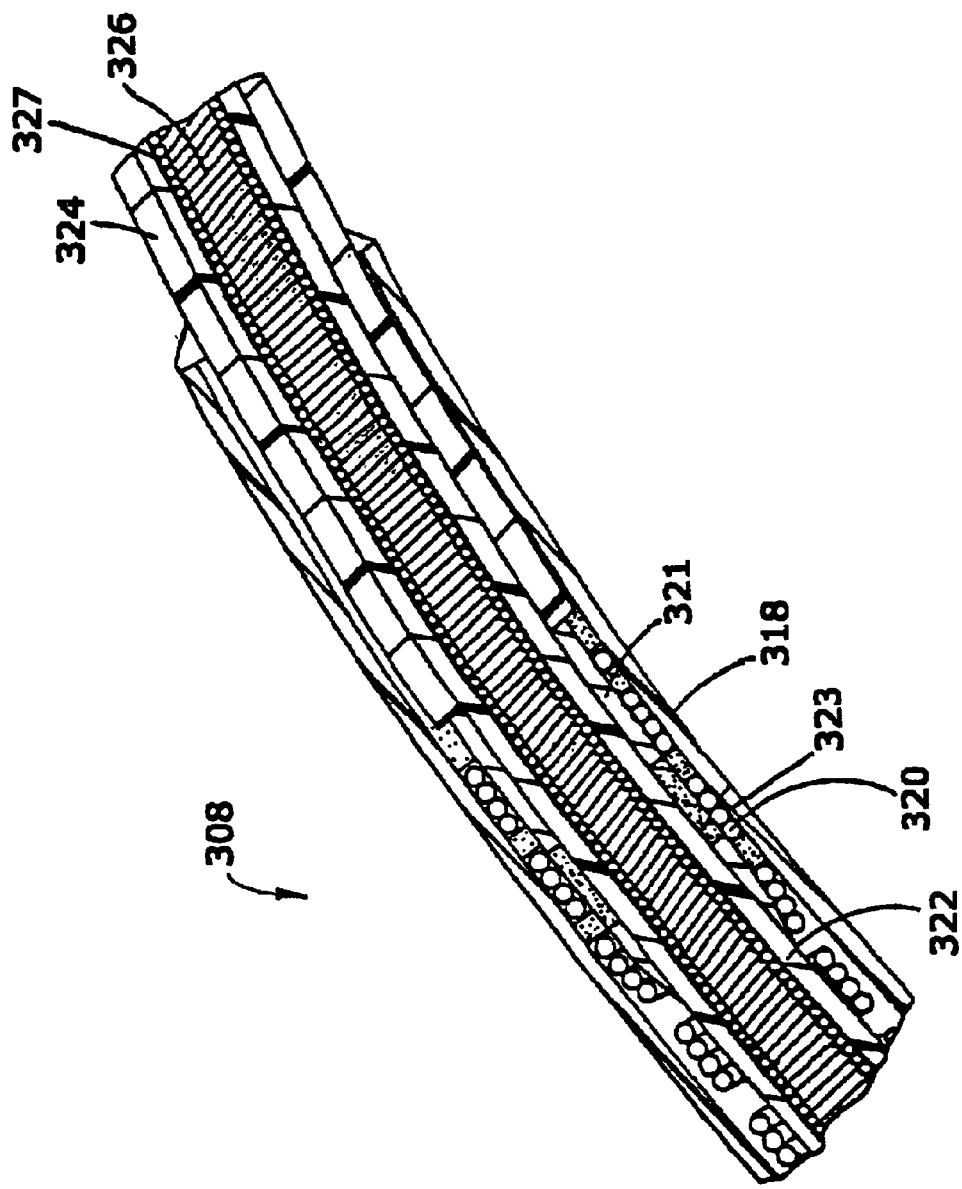

FIG. 13B is a sectional view of the transitional section 308 of catheter assembly 300. Referring to FIG. 13B, and in the preferred embodiment depicted therein, the lead body 300 is provided with a proximal outer polyurethane insulative sheath 318 that extends back to the connector assembly (not shown, but see FIG. 1 of U.S. Pat. No. 6,144,882) and terminates in the transition region 308. Proximal outer polyurethane sheath 318 surrounds the outer coil 320 which in a relaxed state assumes an approximately 45 degree end along its axis and extends proximally therefrom in a generally straight configuration along its axis to a connector ring on a connector assembly (not shown).

The coil 320 terminates at and is welded to a welding sleeve 321 which in turn is mounted around an inner insulative sheath 322. A distal outer sheath 324 and an inner conductor 326 complete the assembly.

One can coat the elements 320 and 326 with nanomagnetic particles coatings 323 and 327 to provide the desired electromagnetic radiation shielding.

Figure 13D:
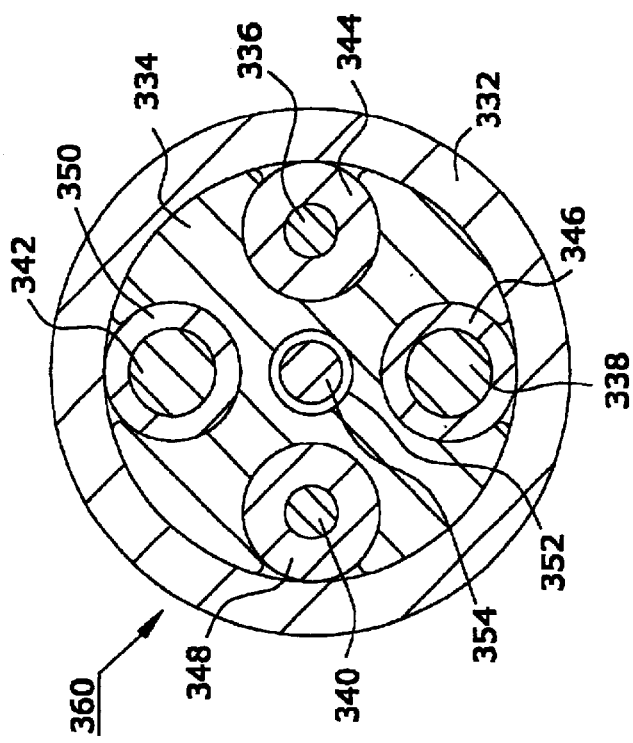
Figure 13C:
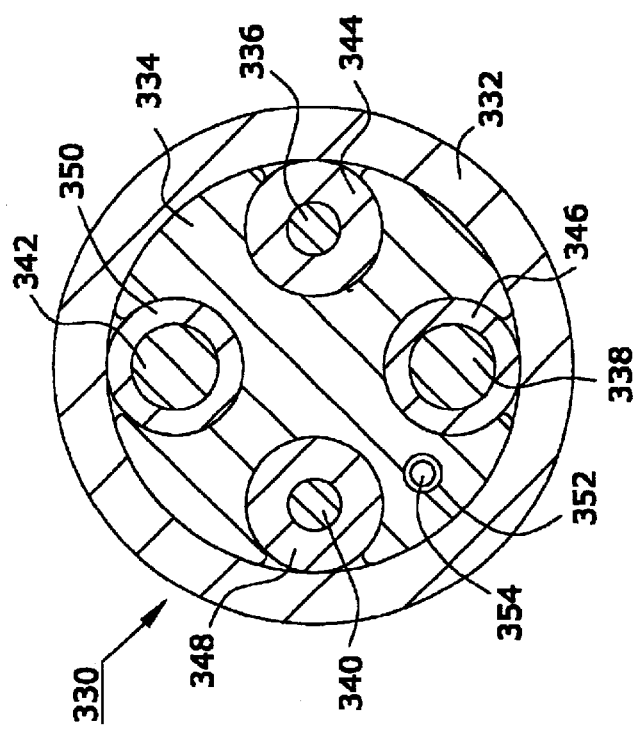
Figure 13E:
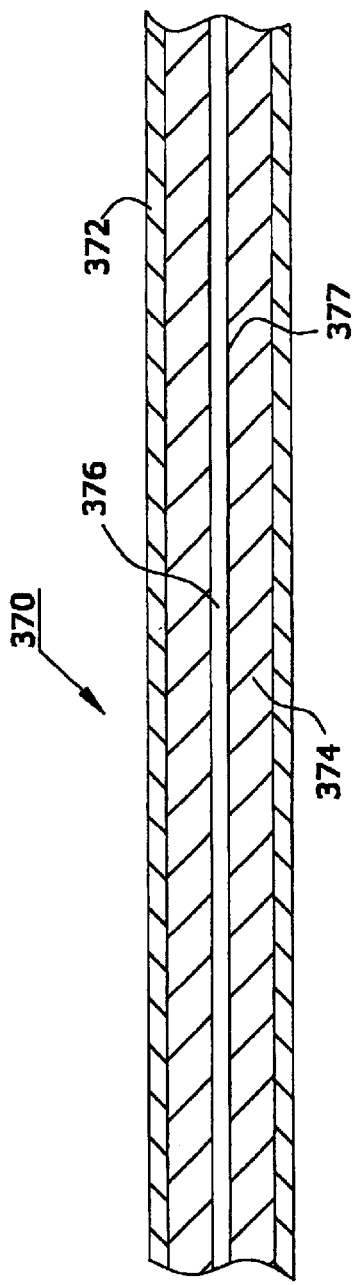

FIGS. 13C, 13D and 13E are conductor assemblies similar to that depicted in U.S. Pat. No. 5,935,159, the entire disclosure of which is hereby incorporated by reference into this specification. Referring to FIG. 13C, it will be seen that conductor assembly 330 is comprised of an outer insulative tube 332, a core 334, conductors 336, 338, 340, and 342, each of which is coated with nanomagnetic coatings 344, 346, 348, and 350. A lumen 352 that, in the embodiment depicted, is disposed off-center extends through the assembly 330. A tensile member 354 is disposed within the lumen 352.

In one embodiment, not shown, nanomagnetic shielding is disposed around the entire assembly 330.

FIG. 13D depicts an assembly similar to that depicted in FIG. 13C but differing therefrom in that the tensile member 354 is substantially in the center of the assembly 360.

FIG. 13E is a sectional view of a conductor assembly 370 comprised of an outer insulating tube 372, a core 374, and a cord 376. In one preferred embodiment, cord 376 is conductive and is coated with nanomagnetic material 377.

Referring again to FIGS. 13A, 13B, and 13C, the nanomagnetic coatings may be applied to mechanical members used to provide leads with desirable physical properties, such as for example desired stiffness and geometry. Although these members are generally not used to conduct electrical stimulation pulses or sensing information, they are for example able to absorb RF energy and heat up.

By way of illustration, the shielded conductors described in FIGS. 13A, 13B, and 13C may be used in the lead designs shown in U.S. Pat. Nos. 6,289,251, 6,285,910, 6,192,280, 6,185,463, 6,178,355, 6,144,882, 6,119,042, 6,096,069, 6,066,166, 6,061,598, 6,040,369, 6,038,463, 6,026,567, 6,018,683, 6,016,436, 6,006,122, 5,999,858, 5,991,668, 5,968,087, 5,968,086, 5,967,977, 5,964,795, 5,957,970, 5,957,967, 5,957,965, 5,954,759, 5,948,015, 5,935,159, 5,897,585, 5,871,530, 5,871,528, 5,853,652, 5,796,044, 5,760,341, 5,702,437, 5,676,694, 5,584,873, 5,522,875, 5,423,881, 5,411,545, 5,354,327, 5,336,254, 5,336,253, 5,324,321, 5,303,704, 5,238,006, 5,217,027, and 5,007,435, the entire disclosure of which is hereby incorporated by reference into this specification.

Figure 14A:
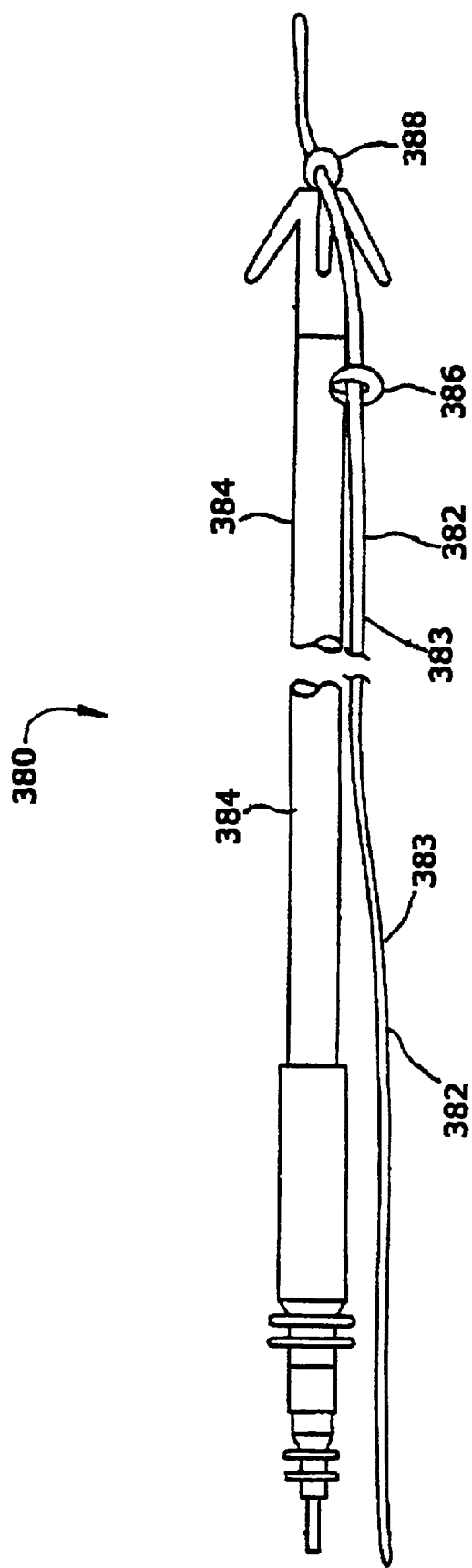
FIG. 14 is a schematic of nanomagnetic coating applied to a lead stylet and lead guide wire.

FIG. 14A is a schematic of an implantable medical lead using a conductor and a distal loop, that is similar to a similar assembly disclosed in U.S. Pat. No. 5,957,967, the entire disclosure of which is hereby incorporated by reference into this specification. Referring to FIG. 14A, the conductor assembly 380 is comprised a guide wire 382, an insulative lead body 384, a loop 386, and a loop 388. The guide wire 382 is preferably coated with nanomagnetic particles 383; and any other conductive parts (not shown) disposed within insulative lead body 384 also are preferably coated with nanomagnetic particles. Thus, e.g., such nanomagnetic coating may be applied to a lead stylet and to lead guide wire used to help position leads under magnetic resonance imaging guidance. Although these members are not used to conduct electrical stimulation pulses or sensing information, they are for example able to absorb radio frequency energy and heat up.

By way of further illustration, the shielded conductors described in FIG. 14A may be used in the lead designs shown in U.S. Pat. Nos. 6,192,280, 6,119,042, 6,040,369, 5,999,858, 5,991,668, 5,964,795, 5,957,967, 5,948,015, 5,935,159, 5,522,875, 5,423,881, 5,411,545, 5,354,327, 5,303,704, the entire disclosure of which is hereby incorporated by reference into this specification.

Figure 14B:
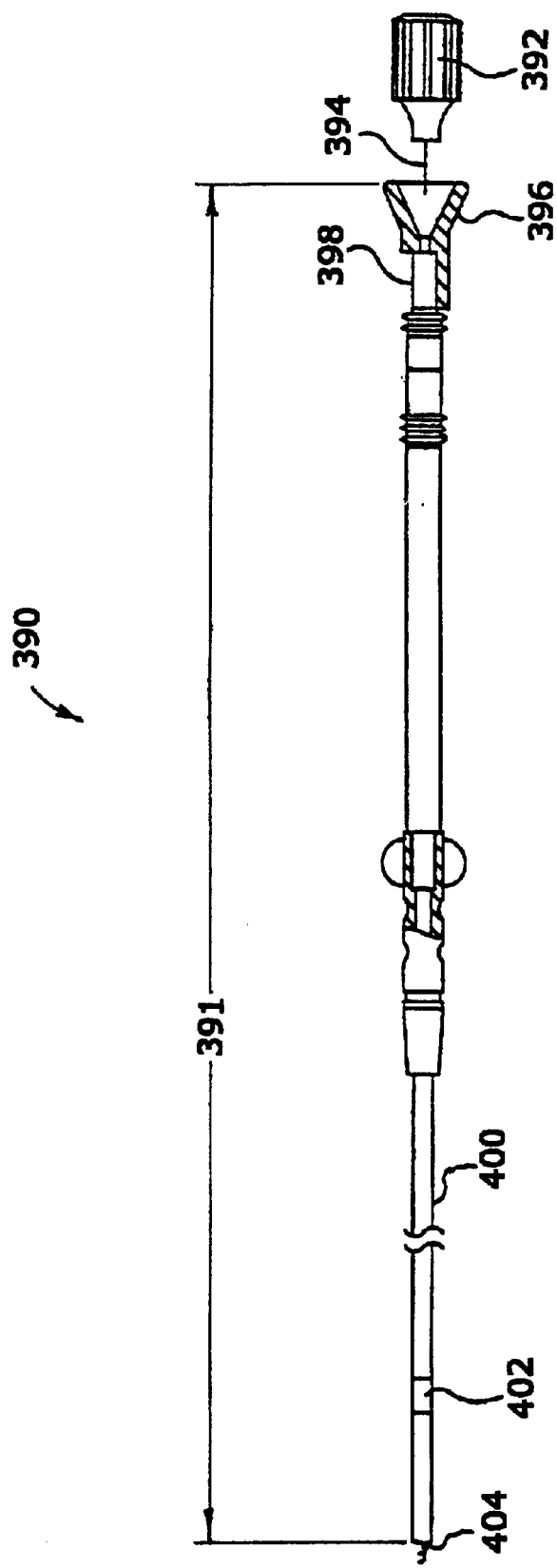

FIG. 14B is a schematic of a medical electrical lead system having a torque transfer stylet assembly 390 similar to the assembly depicted in U.S. Pat. No. 5,522,875, the entire disclosure of which is hereby incorporated by reference into this specification.

Referring to FIG. 14B, it will be seen that assembly 390 is comprised of a knob 392, a distal straight wire section 394, a stylet guide 396, a terminal pin 398, a lead body 400, a ring electrode 402, and a tip electrode 404. The body 390 is preferably flexible, i.e., it has the property of a material that may be flexed or bowed repeatedly without undergoing rupture.

Figure 14C:
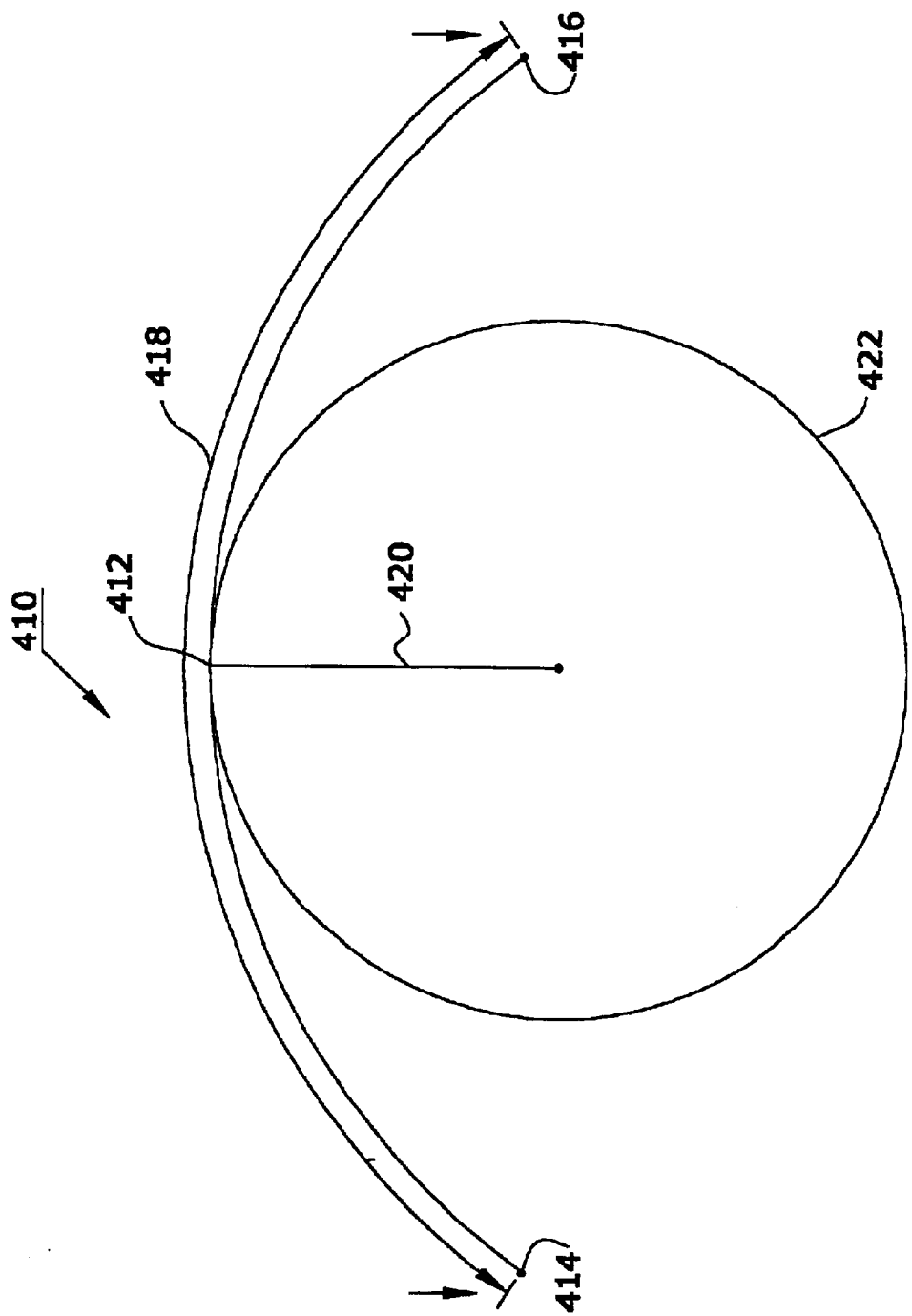

FIG. 14C indicates a conductor 410 that is bent around a midpoint 412 with force being applied at points 414 and 416. The length between points 414 and 416, length 418, is the initial length; and the conductor so bent has an effective radius 420, from which the effective circumference of the bent conductor can be calculated. Flexibility is a function of the ratio of the effective circumference of the conductor to its length. A conductor is flexible within the meaning of this specification when such ratio is less than 1.0.

Referring again to FIG. 14B, total length of assembly 390 is indicated as element 391. As assembly 390 is bent, its effective circumference is always less than the length 391.

Figure 14D:
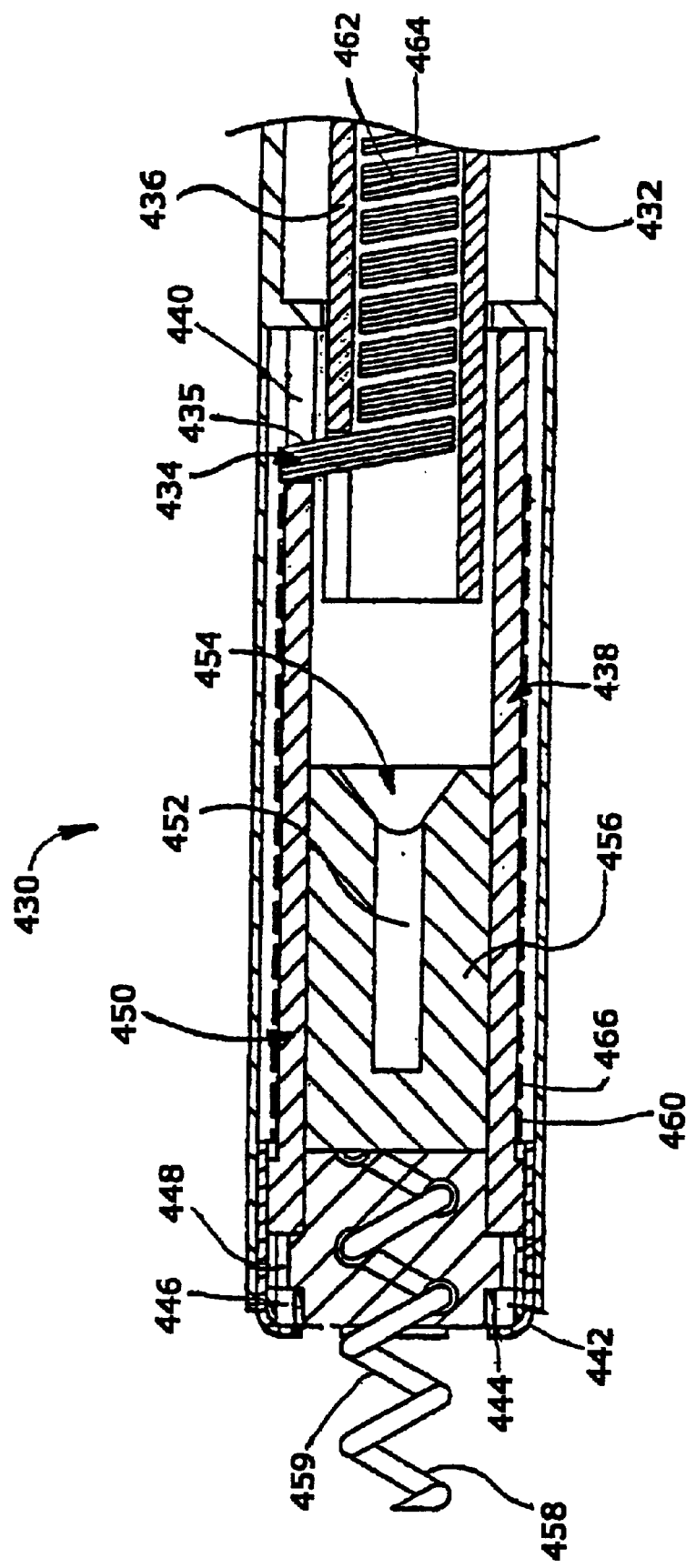

FIG. 14D illustrates a medical electrical lead system having a torque transfer stylet similar to that depicted in FIG. 2b of U.S. Pat. No. 5,522,875, the entire disclosure of which is hereby incorporated by reference into this specification; but it differs therefrom in that one or more of its flexible conductive components is coated with nanomagnetic particles.

Referring to FIG. 14D, a conductor assembly 430 is depicted. This assembly is comprised of tip/ring spacer 432, inner conductor 434, inner insulative sheath 436, cylindrical helix sleeve 438, rectangular slot 440, forward facing tab 442, through holes 444, washer-like polysulfone electrode shim 446, monolithic controlled release device 448, helix assembly 450, axially oriented rectangular slot 452, flare opening 454, stylet socket 456, and pointed tip of helix 458. Flexible Conductors 460 and 462 are preferably coated with nanomagnetic particles 464 and 466. Additionally, in the embodiment depicted, inner conductor 434 is coated with nanomagnetic particle coating 435; and a portion of the pointed tip 458 also may be coated with nanomagnetic particle coating 459.

Figure 14E:
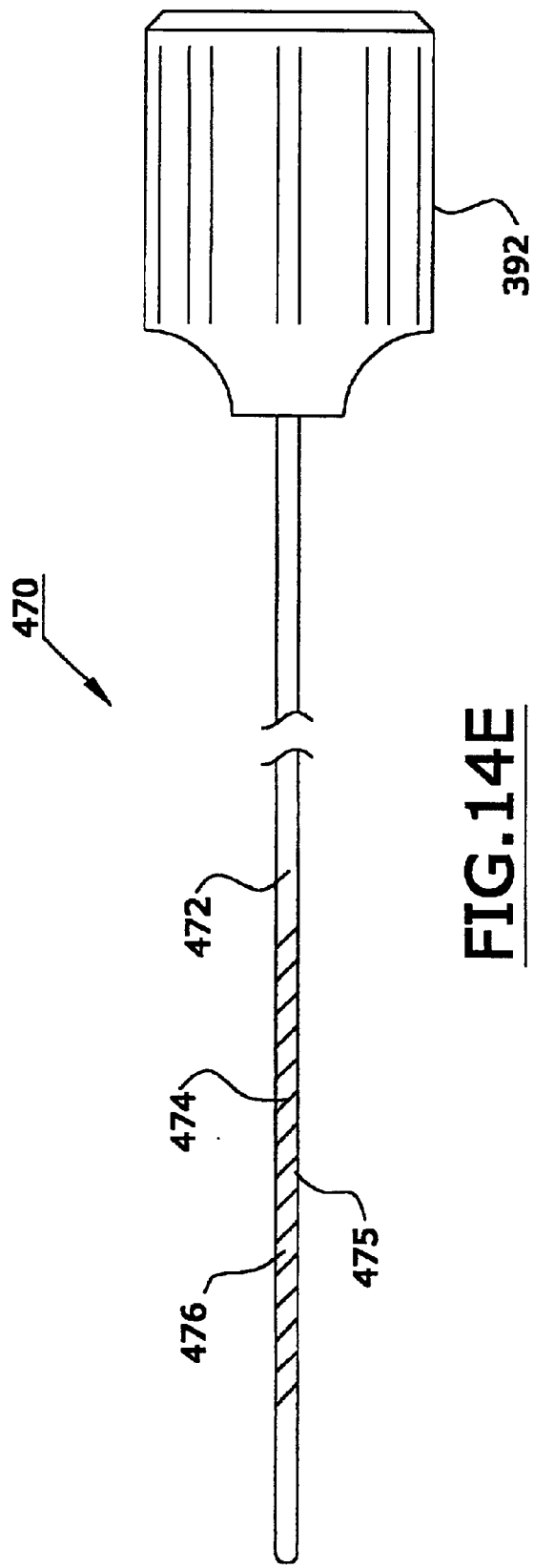

FIG. 14E is a schematic representation of a stylet 470 similar to the stylet depicted in FIG. 7A of U.S. Pat. No. 5,522,875, supra. Stylet 470 is comprised of a proximal section 472, helical torque coil 474, intermediate section 476. The helical torque coil 474 is coated with nanomagnetic particles 475. Additionally, other conductive components of such stylet 470 also may be coated with the nanomagnetic particles.

In general, the nanomagnetic particles, when they form a film with a thickness of about 100 nanometers or larger, produce an article with a specified modulus of elasticity (Young's Modulus). As is known to those skilled in the art, the modulus of elasticity is the ratio of the stress acting on a substance to the strain produced. In general, the nanomagnetic particle coatings and films produced by the process of this invention have a tensile modulus of elasticity of at least about $15 \times 10^6$ pounds per square inch.

Figure 14F:
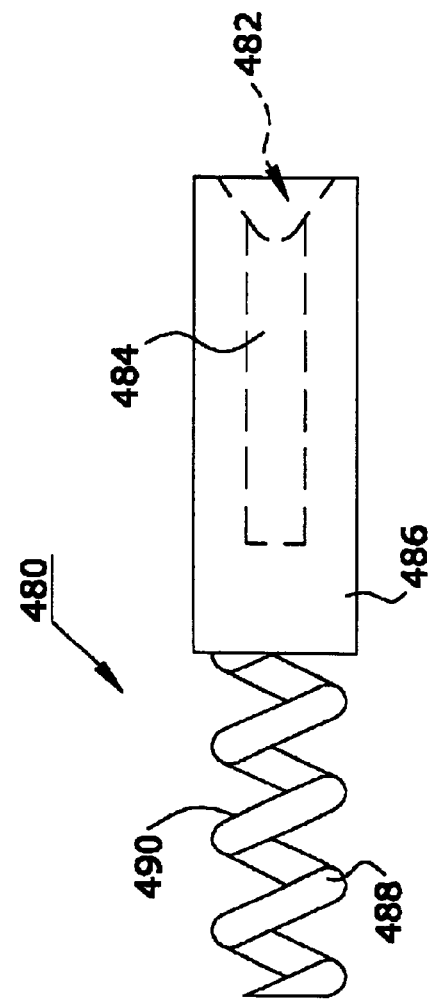

FIG. 14F is a conductor assembly 480 similar to that depicted in FIG. 5 of U.S. Pat. No. 5,522,875, supra. Referring to FIG. 14F, it will be seen that assembly 480 is preferably comprised of a flared opening 482, an axially oriented rectangular slot 484, a stylet socket 486, and a sharp ended helix 488. Helix 488 is partially coated with nanomagnetic particle coating 480.

As is illustrated in FIG. 14A, a nanomagnetic coating may be applied to a steerable wire. Steerable guide wires can be created, for example, by producing differential strain through tension wires electrically exciting piezoelectric elements. Each of these configurations is electrically conductive and susceptible to externally applied electromagnetic fields. The present invention preferably coats these elements with a nanomagnetic coating shield to protect these elements during magnetic resonance imaging-guided installation.

Figure 15A:
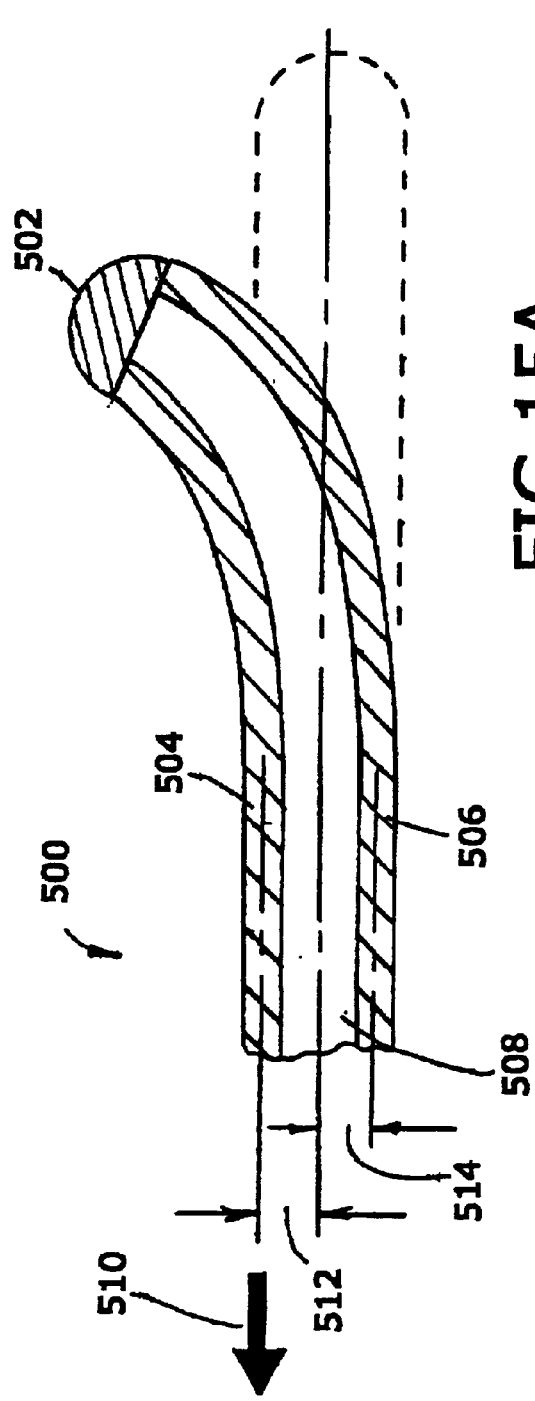
FIG. 15 is a schematic of nanomagnetic particle coated steerable guide wire.
Figure 15B:
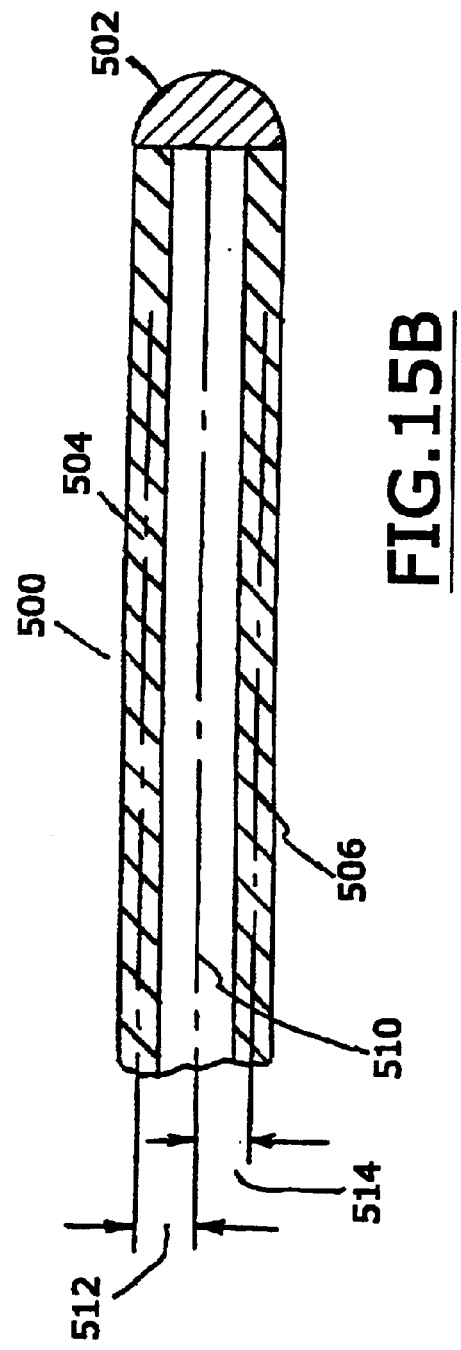

FIG. 15A is a schematic of a steerable guide wire assembly 500 comprised of a tip 502, an upper portion 504, a lower portion 506, and an orifice 508. When the upper portion 504 of assembly 500 is pulled by an external force (not shown) in the direction of arrow 510, the tip 502 is lifted upwardly. Conversely, when the lower portion 506 is pulled in the direction of arrow 510, the tip 502 is moved downwardly. As is indicated in FIG. 15B, when force is applied to neither the upper portion 504 nor the lower portion 506, the assembly 500 remains in a flaccid position. Put another way, only when the offset 512 and the offset 514 are substantially equal will the assembly 500 be in the flaccid position depicted in FIG. 15B. When such offsets 512/514 are not equal, the tip 502 is displaced.

In another embodiment, not illustrated, the displacement of tip 502 is caused by electrical rather than mechanical means using, e.g., piezoelectric elements.

In the preferred embodiment depicted in FIGS. 15A and 15B, the upper portion 504 and the lower portion 506, each of which are preferably conductive wires, are coated with nanomagnetic coatings 505 and 507, respectively.

Referring again to FIGS. 15A and 15B, one or more nanomagnetic coatings may be applied to a lead electrode to help position the lead into proper contact with the tissue or organ to be stimulated or sensed. Although these members are not used to conduct electrical stimulation pulses or sensing information, they are, for example, able to absorb radio frequency energy and heat up. By way of illustration, the shielded conductors described in these Figures may be used in the lead designs shown in U.S. Pat. Nos. 6,006,122 and 5,967,977, the entire disclosure of each of which is hereby incorporated by reference into this specification.

Figure 16A:
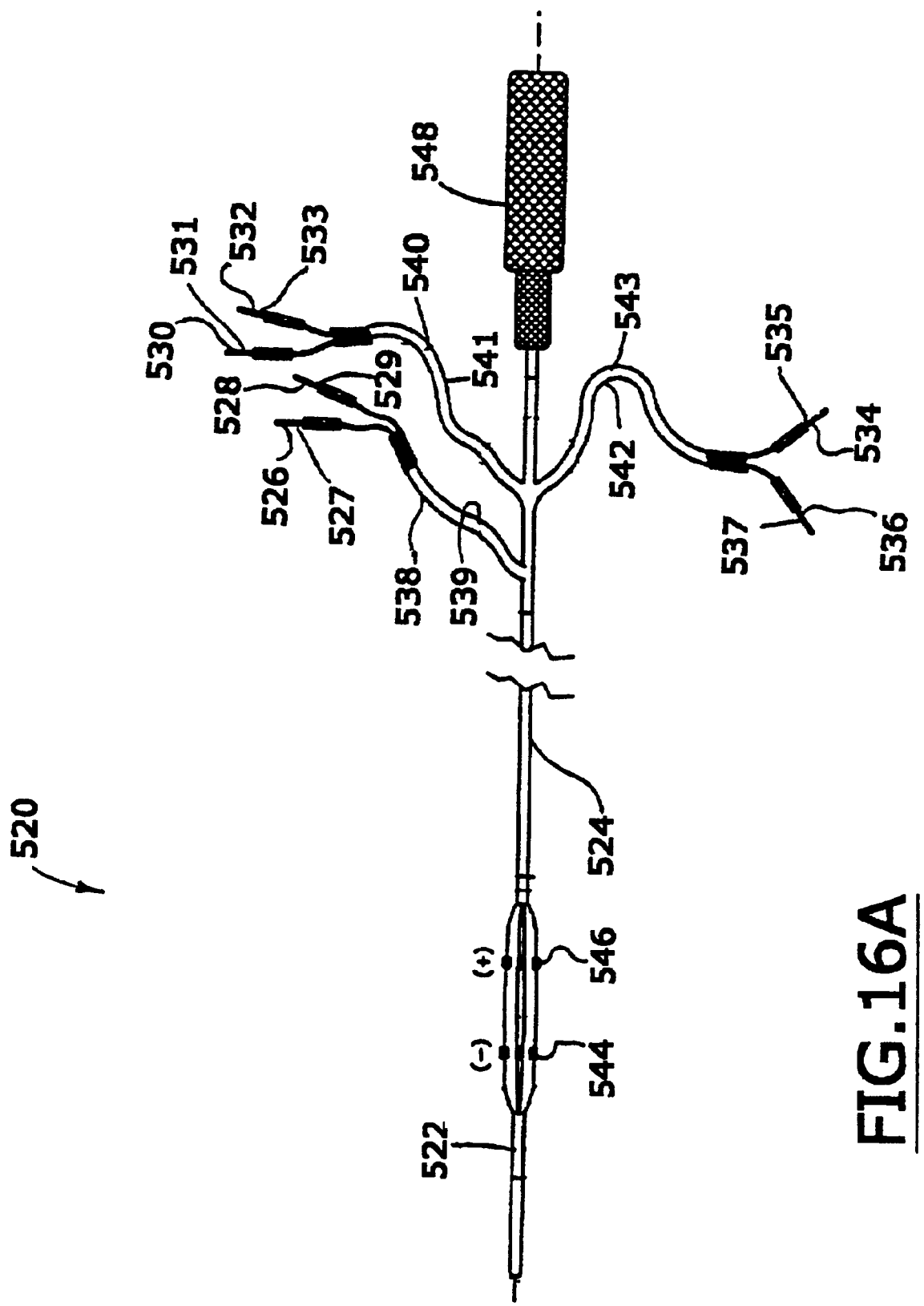
FIG. 16 is a schematic of nanomagnetic particle coated lead electrode positioning device.

FIG. 16A is a transesophageal medical lead 520 similar to the device depicted in U.S. Pat. No. 5,967,977 (see FIG. 1), the entire disclosure of which is hereby incorporated by reference into this specification. Referring to FIG. 16A, it will be seen that lead 520 is comprised of a distal end 522, a lead body 524, external connectors 526, 528, 530, 532, 534, and 536, electrical conductors 538, 540, and 542, electrodes 544 and 546, and a knob 548. The external conductors 526, 528, 530, 532, 534, and 536 are coated with nanomagnetic particle coatings 527, 529, 531, 533, 535, and 537, respectively. The electrical conductors 538, 540, and 542 are also preferably coated with nanomagnetic coatings, 539, 541, and 543, respectively. In one embodiment, electrodes 544 and 546 are coated with nanomagnetic coatings 545 and 547, respectively. In addition, any other conductive materials within the assembly also may be coated with nanomagnetic particles.

Figure 16B:
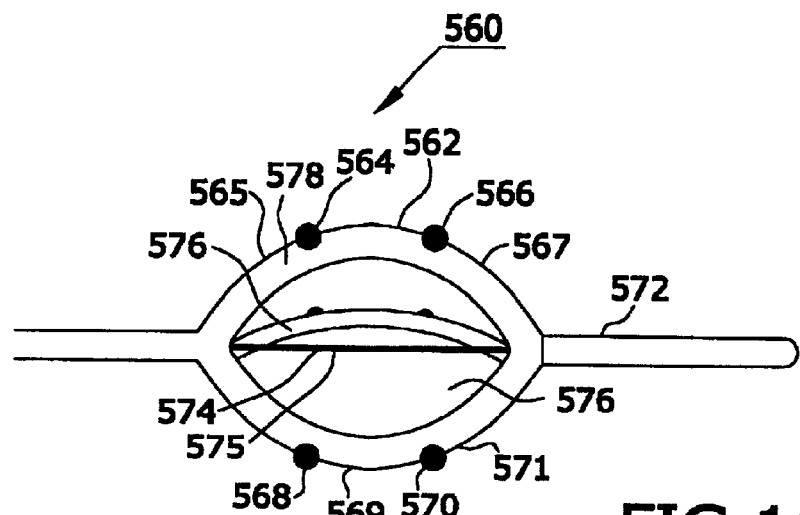

FIG. 16B is a medical lead assembly 560 that is similar to the medical lead depicted in FIG. 2(a) of U.S. Pat. No. 5,967,977, supra. Referring to lead assembly 560, it will be seen that such assembly 560 is comprised of an arm 562, electrodes 564, 566, 568, and 570, and distal end 572. A tension element 574 is disposed within an opening 576 and used to expand the lead assembly 560 radially and to collapse the lead assembly axially in the manner described in such patent; as indicated, the tension element 574 may be move the electrode assembly from position 576 to position 578, and vice versa. The electrodes 564, 566, 568, and 570 are coated with nanomagnetic particle coatings 565, 567, 569, and 571, The tension element 574 is preferably coated with nanomagnetic coating 575.

Figure 16C:
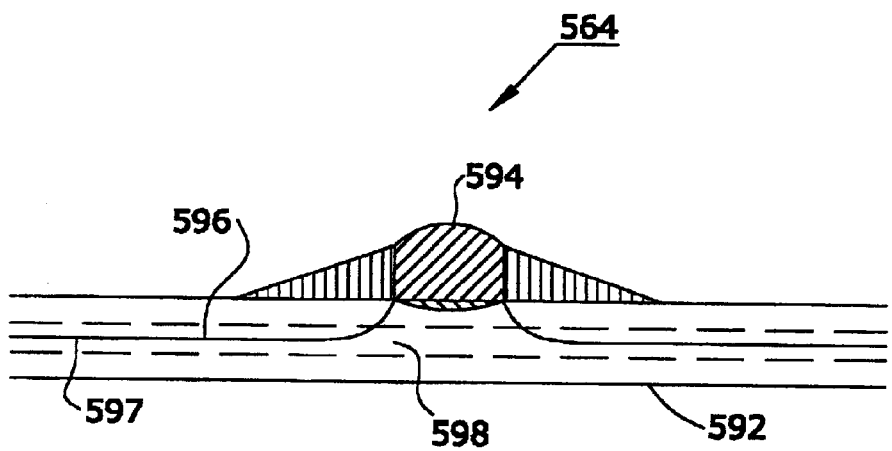

FIG. 16C is a schematic view of electrode 564, and/or a similar electrode, that is similar to the lead assembly depicted in FIG. 8A of U.S. Pat. No. 5,967,977, supra. Referring to FIG. 16C, it will be seen that lead assembly 590 is comprised of an arm 592, an electrode 594, an insulated electrical conductor 596 coated with nanomagnetic material 597. a lumen 598.

Figure 16D:
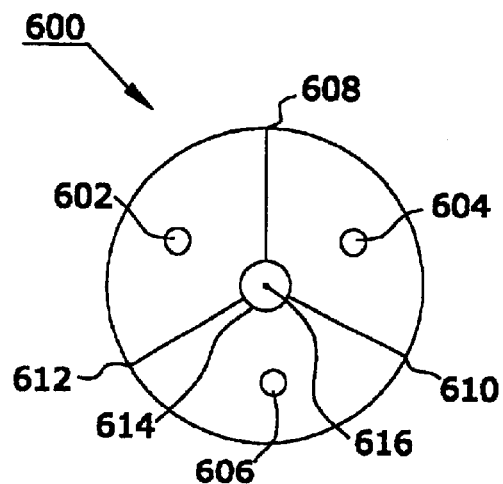

FIG. 16D is a schematic view of a lead assembly 600 that is similar to the lead assembly depicted in FIG. 6B of U.S. Pat. No. 5,967,977, supra. Referring to FIG. 16D, it will be seen that lead assembly 600 is comprised of lumens 602, 604, and 606, that are formed by cuts 608, 610, and 612. The lead assembly also is comprised 614 and an imaginary axis 616. Conductive elements within assembly 600 are coated with nanomagnetic material.

FIG. 16E is a schematic of an electrode assembly 620 disposed adjacent to biological tissue 622. The assembly 620 is comprised of a compression member 624, electrode 626, and electrode 628. The compression member 624 is preferably anchored at point 630. When catheter 632 is pushed in the direction of arrow 634, it exerts force upon compression member 624, causing it to buckle and assume the position depicted in FIG. 16F, after moving in the direction of arrow 636. This movement causes electrodes 626 and 628 to contact biological tissue 622.

In the embodiment depicted in FIGS. 17A, 17B, 17C, and 17D, conductor assemblies similar to those depicted in U.S. Pat. No. 5,871,530 are illustrated; the entire disclosure of each of these United States patents is hereby incorporated by reference into this specification.

Figure 17A:
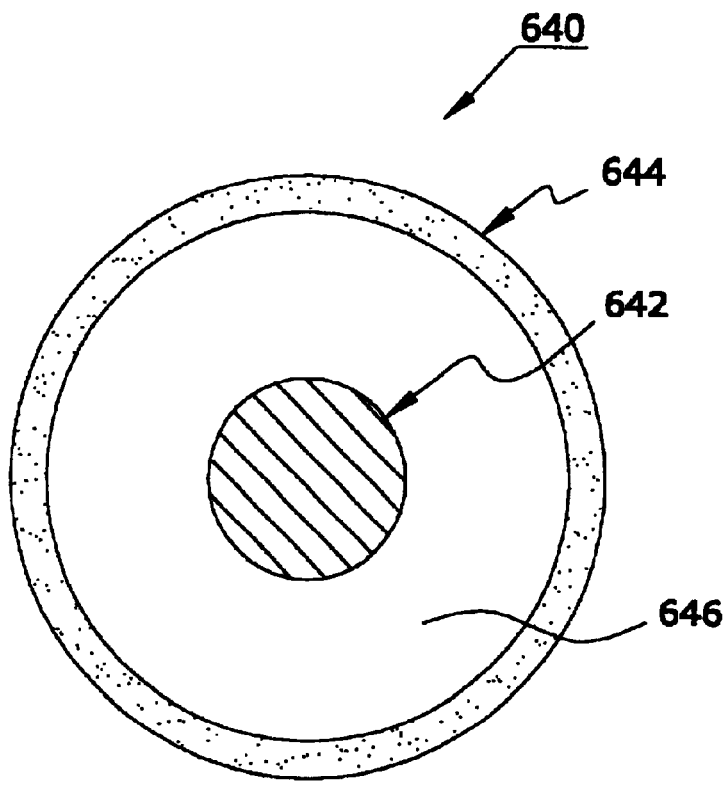
FIG. 17 is a schematic nanomagnetic particle coated sheath.

Referring to FIG. 17A, conductor assembly 640 is comprised of a conductor assembly 642 disposed within a magnetic coating 644. In the embodiment depicted in FIG. 17A, insulating material 646, such as plastic, may be disposed between the conductor assembly 642 and the magnetic coating 644.

Figure 17B:
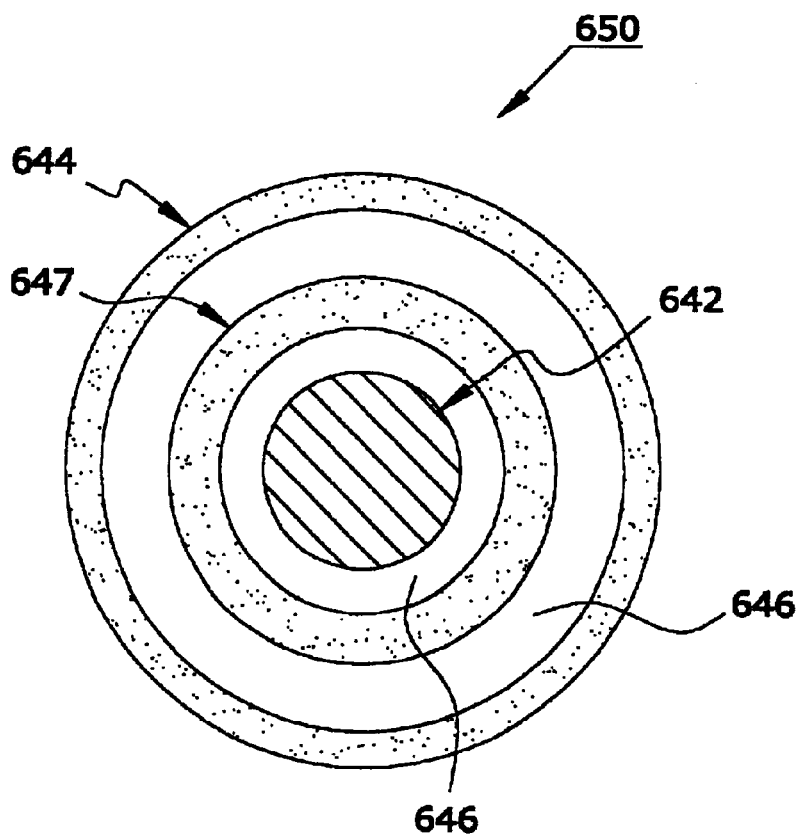

The assembly 650 depicted in FIG. 17B is similar to the assembly depicted in FIG. 17A but differs therefrom it contains an intermediate nanomagnetic coating layer 647.

Figure 17C:
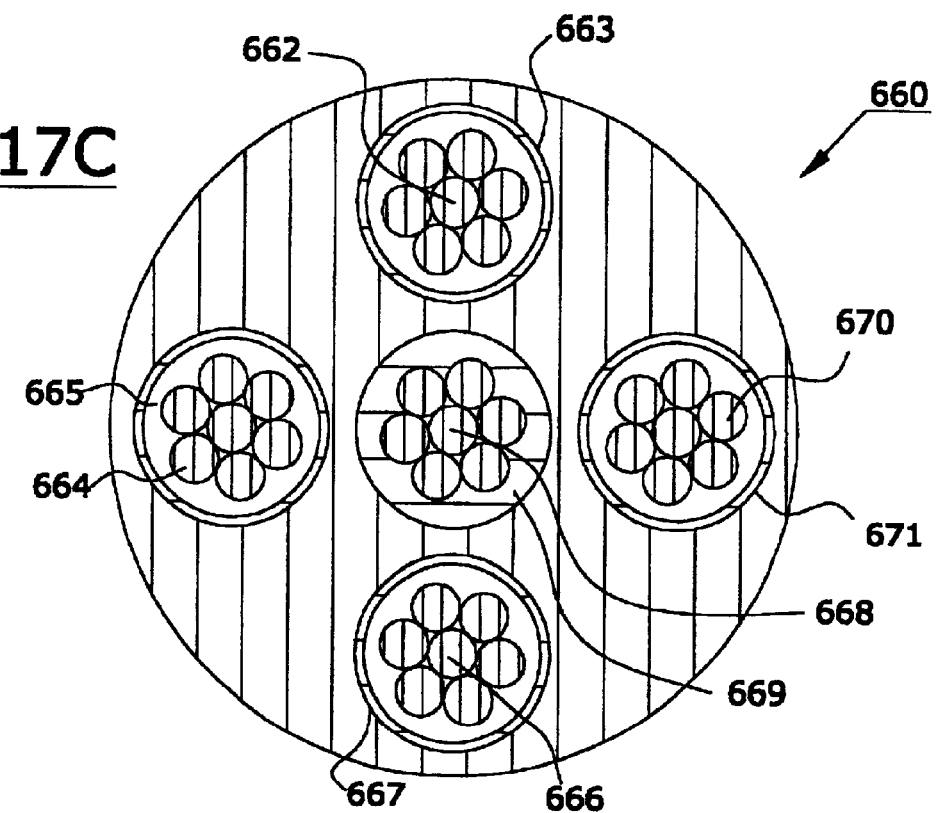

The assembly 660 depicted in FIG. 17C is similar to the assembly depicted in FIG. 17A with the exception that it comprises a multiplicity of conductor assemblies 662, 664, 666, 668, and 670. The conductor assemblies 662, 664, 666, 668, and 670 are coated with nanomagnetic materials 663, 665, 667, 669, and 671.

Figure 17D:
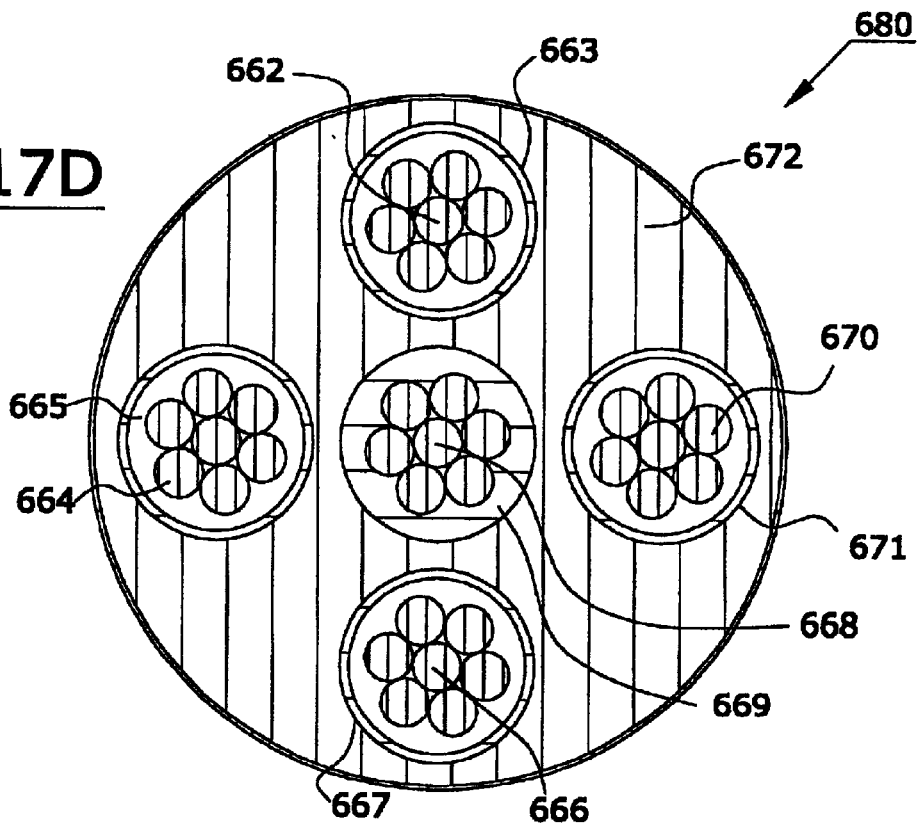

The assembly 680 depicted in FIG. 17D is similar to the assembly depicted in FIG. 17C with the exception that the assembly 660 is coated with nanomagnetic material 672.

Figure 17E:
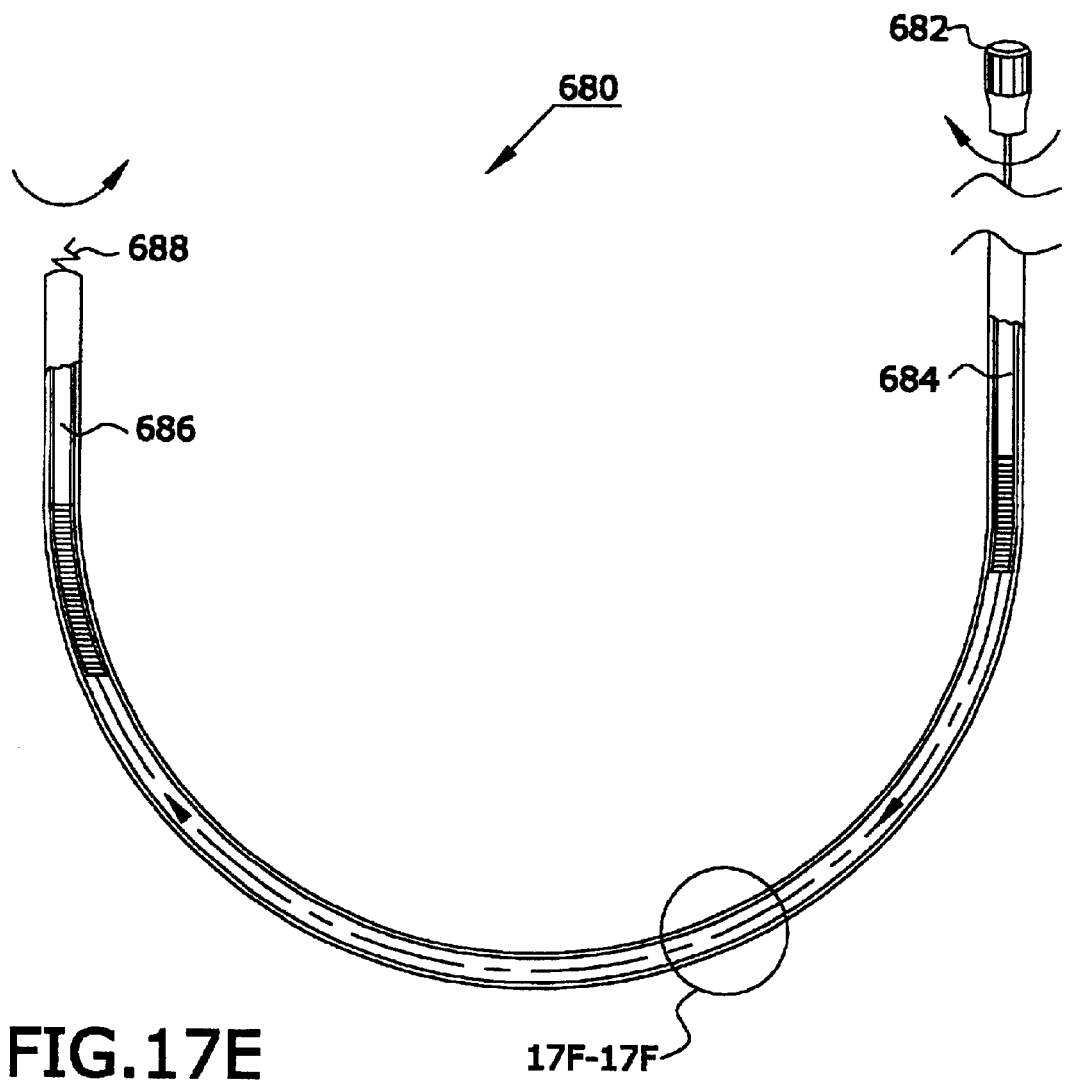

In FIG. 17E, a torque stylet 680 used to activate a helix in a bent lead is illustrated. FIG. 17E is similar to that depicted in FIG. 14A of U.S. Pat. No. 5,522,875, with the exception that the conductive components in the stylet are coated with the nanomagnetic materials. The entire disclosure of each of these United States patents is hereby incorporated by reference into this specification. In FIG. 17E, the stylet 680 is comprised of a knob 682, a proximal wire section 684, a distal portion 686, a fixation assembly 688.

Figure 17F:
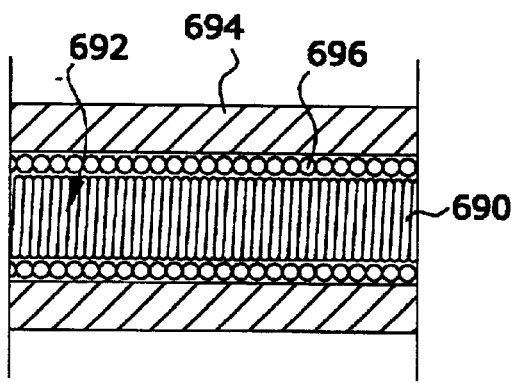

In FIG. 17F, a portion of FIG. 17E is illustrated FIG. 17F is similar to that depicted in FIG. 14B of U.S. Pat. No. 5,522,875, with the exception that the conductive components in the stylet are coated with the nanomagnetic materials. The entire disclosure of each of these United States patents is hereby incorporated by reference into this specification. FIG. 17F is comprised of a helical torque coil 690, an intermediate section 692, an outer insulative sheath 694, and a conductor 696.

Referring back to FIG. 17A, a schematic is illustrated for an assembly in which nanomagnetic particles are coated on a sheath, to shield uncoated conductors positioned within the sheath. Multiple concentrically positioned sheaths are also used to provide additional protection of uncoated conductors positioned within the sheaths. In one embodiment, this sheath is constructed of a tube impregnated with nanomagnetic particles, or a braided wire mesh coated with nanomagnetic particles. In one embodiment, an internally positioned conductors is free to move, e.g., free to rotate or translate. In another embodiment, the motion of the active fixation electrode is controlled. By way of illustration, the shielded conductors described in FIG. 17A may be used in the lead designs illustrated in U.S. Pat. Nos. 6,289,251, 6,285,910, 6,192,280, 6,185,463, 6,178,355, 6,144,882, 6,119,042, 6,096,069, 6,066,166, 6,061,598, 6,040,369, 6,038,463, 6,026,567, 6,018,683, 6,016,436, 6,006,122, 5,999,858, 5,991,668, 5,968,087, 5,968,086, 5,967,977, 5,964,795, 5,957,970, 5,957,967, 5,957,965, 5,954,759, 5,948,015, 5,935,159, 5,897,585, 5,871,530, 5,871,528, 5,853,652, 5,796,044, 5,760,341, 5,702,437, 5,676,694, 5,584,873, 5,522,875, 5,423,881, 5,411,545, 5,354,327, 5,336,254, 5,336,253, 5,324,321, 5,303,704, 5,238,006, 5,217,027, and 5,007,435. The entire disclosure of which is hereby incorporated by reference into this specification.

Figure 18:
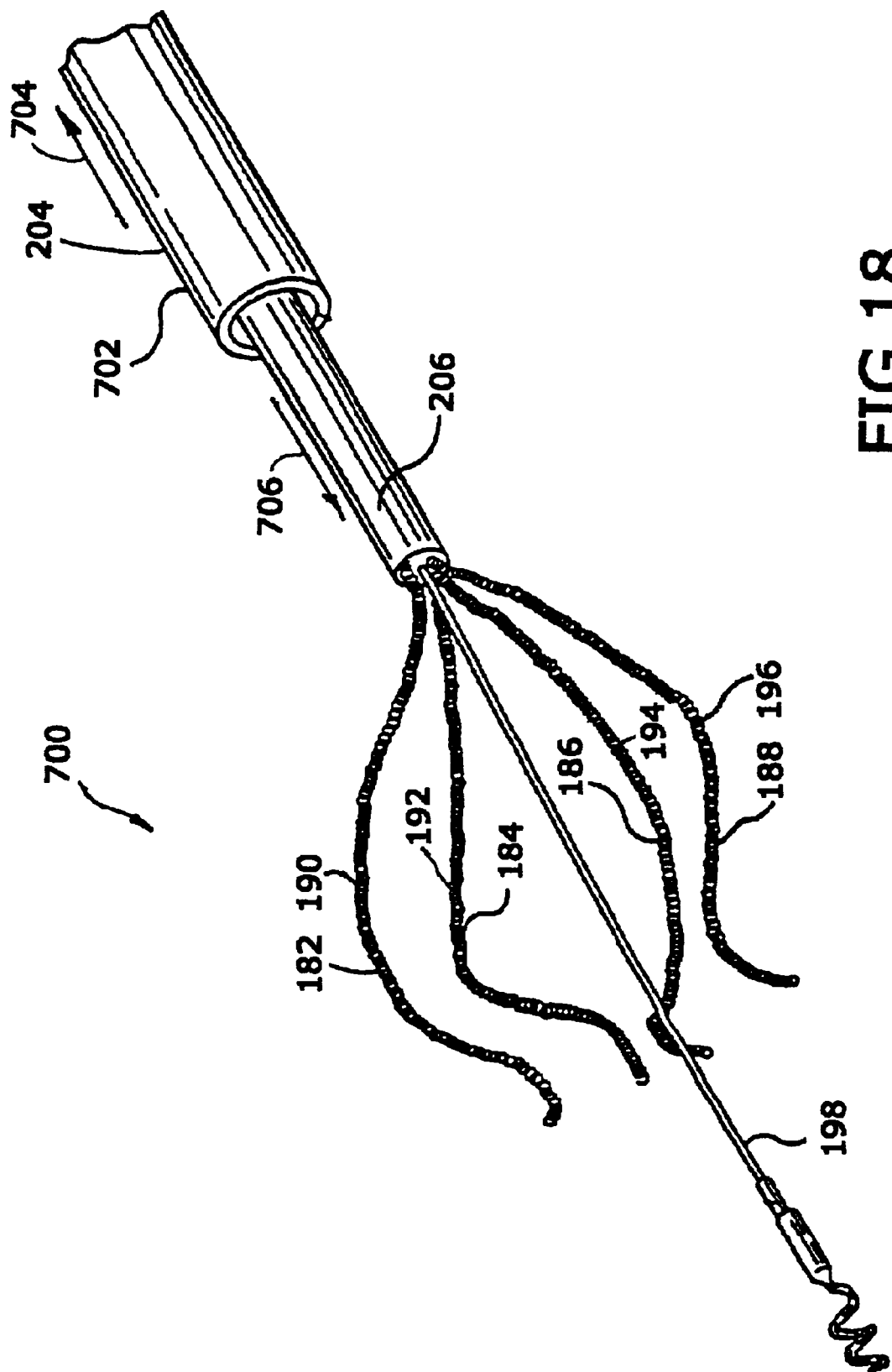
FIG. 18 is a schematic of extensible nanomagnetic coated sheath assembly.

FIG. 18 is a schematic of an extensible assembly 700, with nanomagnetic coating 702 on the catheter 204. In another embodiment (not shown), nanomagnetic coating is coated inside of the catheter 204. The extensible assembly 700 is similar to the assembly 202 depicted in FIG. 9B, with the exception that there is a relative motion between the catheter 204 and sheath 206. The relative motion is illustrated by arrows 704 and 706. In one embodiment, catheter 204 covers sheath 206 completely. In another embodiment, catheter 204 does not cover sheath 206. In yet another embodiment, catheter 204 partially covers sheath 206. In one embodiment, the assembly 700 consists of nanomagnetically coated catheter 204 and sheath 206, that translate axially with respect to one another. In a preferred embodiment, the extended position covers the internally positioned uncoated conductors, and would be used for example during MRI-guided installation. In yet another preferred embodiment, when in the retracted position, the uncoated conductors are exposed to enable contact with the tissue or organ to be stimulated or sensed. By way of illustration, the shielded conductors described in FIG. 18 may be used in the lead designs shown in U.S. Pat. Nos. 6,178,355, 5,967,977, 5,897,585, and 5,871,530. The entire disclosure of which is hereby incorporated by reference into this specification.

FIG. 18A is a schematic diagram of a conductor assembly 708. This assembly 708 is a modified configuration of conductors 182/184/186/188 in FIGS. 18 and 9B. In one embodiment, the assembly 708 is a modified configuration of conductor 126 in FIG. 7A. In another embodiment, the assembly 708 is a modified configuration of conductor 132 in FIG. 7B. Referring back to FIG. 18A, the conductor assembly 708 is comprised of rectangular-shaped sections 710, 712, 714, 716, and 718. The sections 710 and 712 are separated to illustrated the rectangular nature of the conductor assembly.

Figure 19A:
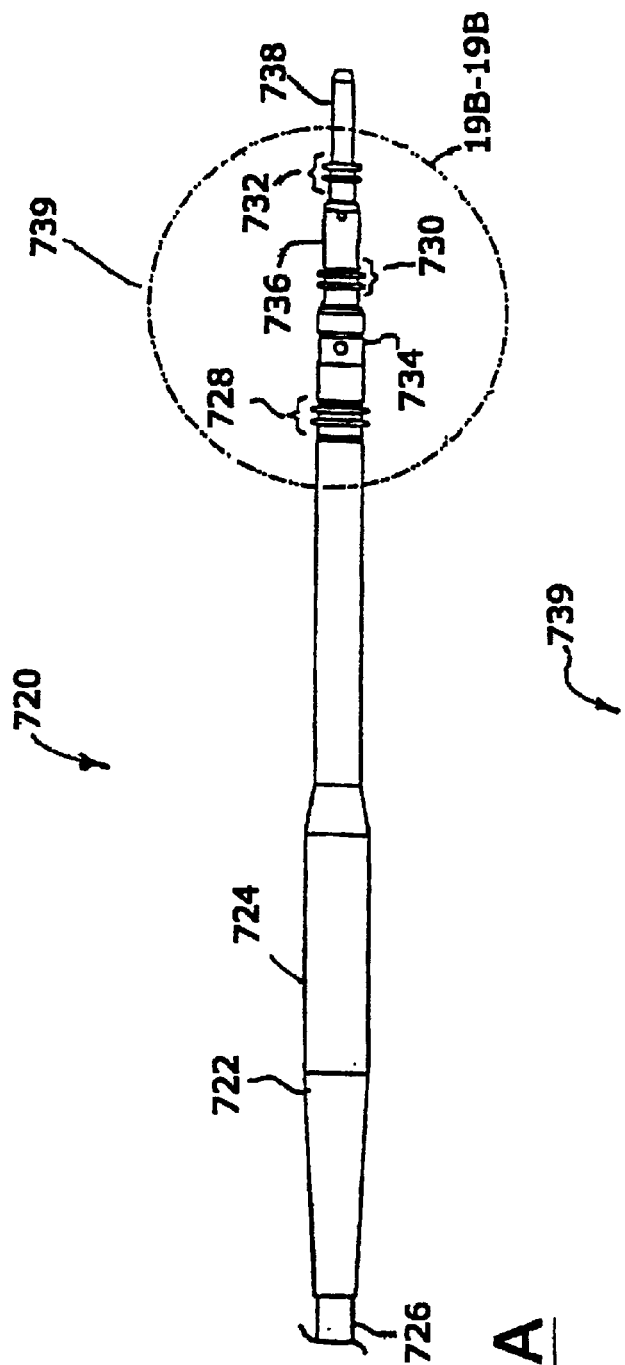
FIG. 19 is a schematic nanomagnetic coating applied to a lead-pulse generator interface.
Figure 19B:
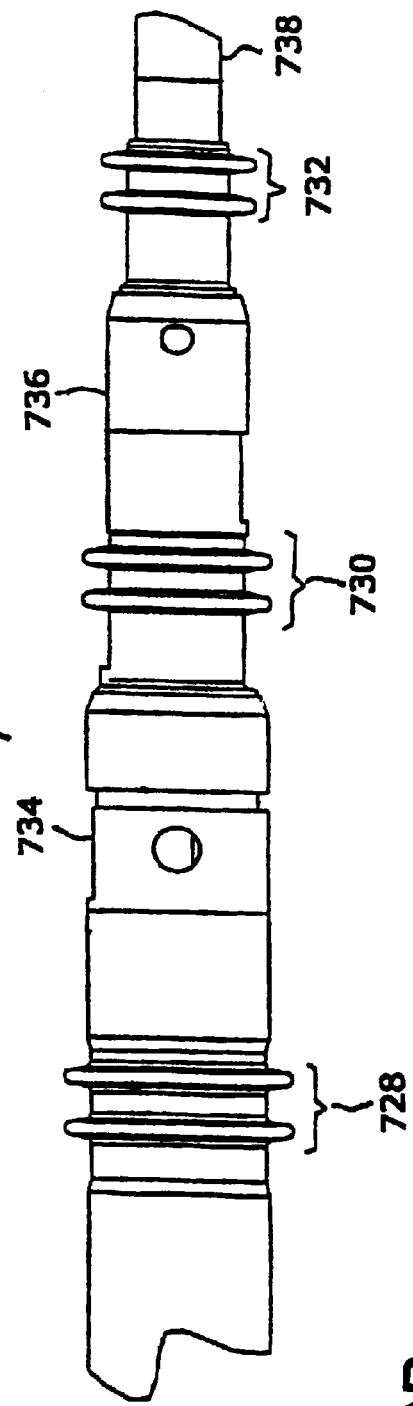

FIG. 19A is a schematic diagram of a proximal lead assembly 720. The assembly 720 is similar to the medical electrical lead disclosed in U.S. Pat. No. 6,096,069, with the exception that the conductive components are coated with nanomagnetic materials. The entire disclosure of each of these United States patents is hereby incorporated by reference into this specification. In FIG. 19A, lead assembly 720 is comprised of an outer insulative sheath 722, a nanomagnetic coating 724, a catheter 726, a subassembly of sealing rings 728, a subassembly of sealing rings 730, a subassembly of sealing rings 732, and electrodes 734/736/738. FIG. 19B is a blow-up diagram of FIG. 19A, in which an adapter subassembly 739 is illustrated.

Figure 19C:
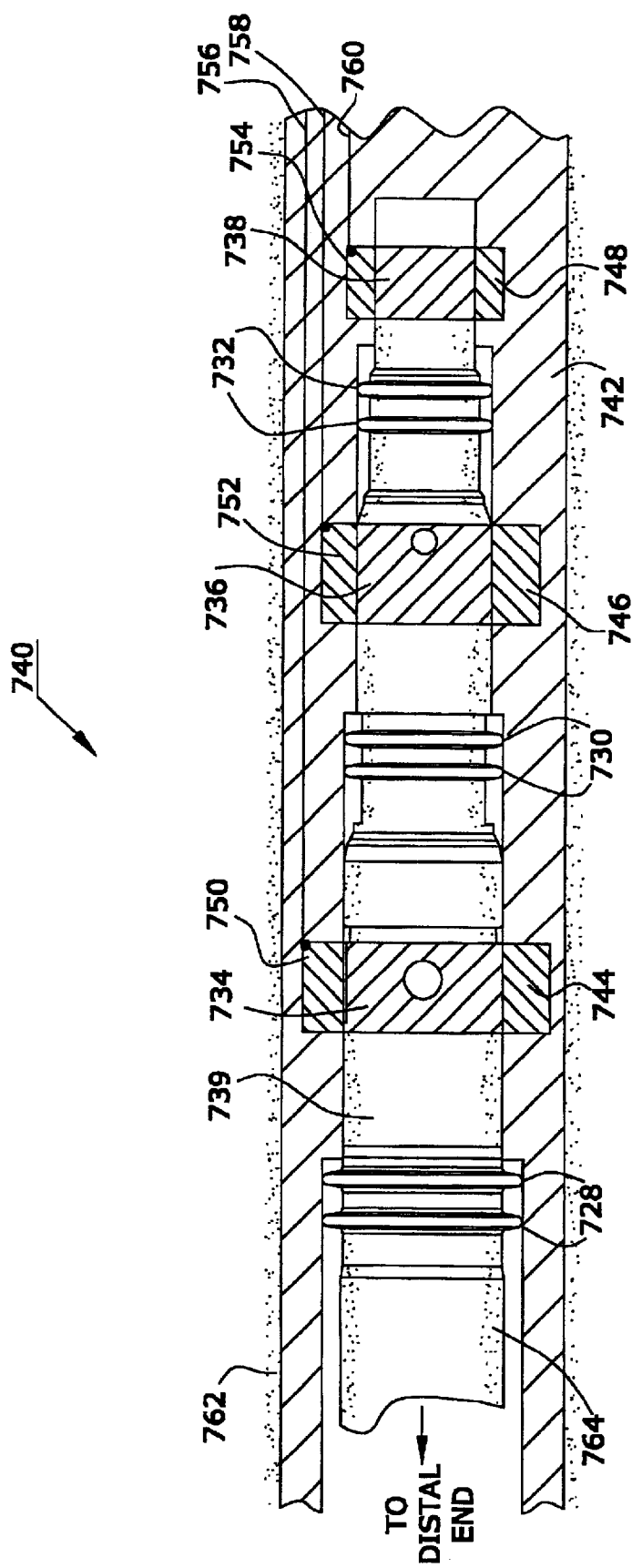

FIG. 19C is a diagram of a lead-pulse generator interface assembly 740. This assembly 740 is comprised of two main parts. One of the parts is a shielded lead connector 742, which has a receptacle configuration. The other part is the adapter subassembly 739, which is already illustrated in FIGS. 19A and 19B. Furthermore, the subassemblies 728/730/732 in FIG. 19C are the same as subassemblies 728/730/732 in FIGS. 19A and 19B.

Referring back to FIG. 19C, electrodes 734/736/738 are shaded. Those electrodes 734/736/738 are the same as the electrodes 734/736/738 illustrated in FIGS. 19A and 19B. The electrodes 734, 736, and 738 are in contact with electrodes 744, 746, and 748, respectively. That is, electrode 734 is in contact with 744. Electrode 736 is in contact with 746. Electrode 738 is in contact with 748. Near the contacting points 750, 752, and 754, electrical leads 756, 758, and 760 are connected. The leads 756/758/760 are connected to a pulse generator (not shown).

Referring back again to FIG. 19C, nanomagnetic coatings 762/764 are applied over the outer surface of the shielded lead connector 742 and the adapter subassembly 739.

By way of illustration, the shielded conductors described in FIGS. 19A/19B/19C may be used in the lead designs shown in U.S. Pat. Nos. 6,289,251, 6,285,910, 6,192,280, 6,185,463, 6,178,355, 6,144,882, 6,119,042, 6,096,069, 6,066,166, 6,061,598, 6,040,369, 6,038,463, 6,026,567, 6,018,683, 6,016,436, 6,006,122, 5,999,858, 5,991,668, 5,968,087, 5,968,086, 5,967,977, 5,964,795, 5,957,970, 5,957,967, 5,957,965, 5,954,759, 5,948,015, 5,935,159, 5,897,585, 5,871,530, 5,871,528, 5,853,652, 5,796,044, 5,760,341, 5,702,437, 5,676,694, 5,584,873, 5,522,875, 5,423,881, 5,411,545, 5,354,327, 5,336,254, 5,336,253, 5,324,321, 5,303,704, 5,238,006, 5,217,027, and 5,007,435. The entire disclosure of which is hereby incorporated by reference into this specification.

It is to be understood that the aforementioned description is illustrative only and that changes can be made in the apparatus, in the ingredients and their proportions, and in the sequence of combinations and process steps, as well as in other aspects of the invention discussed herein, without departing from the scope of the invention as defined in the following claims.

We claim:

1. A conductor assembly comprised of a first flexible conductor and a first layer of nanomagnetic material disposed around said first flexible conductor, wherein:
   (a) said first layer of nanomagnetic material has a tensile modulus of elasticity of at least about $15 \times 10^6$ pounds per square inch;
   (b) said nanomagnetic material has an average particle size of less than 100 nanometers; and
   (c) said first layer of nanomagnetic material has a saturation magnetization of at least about 20,000 Gauss and a thickness of less than about 2 microns.

2. The conductor assembly as recited in claim 1, wherein said conductor assembly is flexible, having a bend radius of less than 2 centimeters.

3. The conductor assembly as recited in claim 1, wherein said first layer of nanomagnetic material has a saturation magnetization of at least 24,000 Gauss.

4. The conductor assembly as recited in claim 3, wherein said conductor assembly is comprised of 7 flexible conductors, each of which has a layer of said nanomagnetic material disposed around it.

5. The conductor assembly as recited in claim 3, wherein a biocompatible sheath is disposed around said first flexible conductor and said first layer of nanomagnetic material.

6. The conductor assembly as recited in claim 5, wherein a second layer of nanomagnetic material is disposed around said biocompatible sheath.

7. The conductor assembly as recited in claim 3, wherein said first flexible conductor is a modfilar conductor.

8. The conductor assembly as recited in claim 7, wherein said first flexible conductor is a multifilar conductor.

9. The conductor assembly as recited in claim 8, further comprising a second flexible monofilar conductor.

10. The conductor assembly as recited in claim 9 wherein said multifilar conductor is disposed outside of said monfilar conductor.

11. The conductor assembly as recited in claim 3, wherein said first flexible conductor is coated with said first layer of nanomagnetic material.

12. The conductor assembly as recited in claim 11, wherein said coating of said first layer of nanomagnetic material on said first flexible conductor is continuous.

13. The conductor assembly as recited in claim 11, wherein said coating of said first layer of nanomagnetic material on said first flexible conductor is discontinuous.

14. The conductor assembly as recited in claim 13, wherein said coating of said first layer of nanomagnetic material on said first flexible conductor is discontinuous along the axial dimension of said first flexible conductor.

15. The conductor assembly as recited in claim 11, wherein said multifilar conductor is disposed inside of said monofilar conductor.

16. The conductor assembly as recited in claim 1, wherein said conductor assembly further comprises a centrally disposed pacing lead.

17. The conductor assembly as recited in claim 1, further comprising a catheter connected to said first flexible conductor.

18. The conductor assembly as recited in claim 1, further comprising an electrode connected to said first flexible conductor.

19. The conductor assembly as recited in claim 1, further comprising electric circuitry connected to said first flexible conductor.

20. The conductor assembly as recited in claim 19, further comprising a second layer of nanomagnetic material disposed around said electric circuitry.

* * * * *